(12) United States Patent
Holwitt

(10) Patent No.: US 6,379,900 B1
(45) Date of Patent: Apr. 30, 2002

(54) COMPOSITIONS AND METHODS OF USE OF 8-NITROGUANINE

(75) Inventor: Eric A. Holwitt, San Antonio, TX (US)

(73) Assignee: Conceptual Mindworks, Inc., San Antonio, TX (US)

( * ) Notice: Subject to any disclaimer, the term of this patent is extended or adjusted under 35 U.S.C. 154(b) by 0 days.

(21) Appl. No.: 09/850,646

(22) Filed: May 7, 2001

Related U.S. Application Data

(60) Provisional application No. 60/203,062, filed on May 9, 2000.

(51) Int. Cl.$^7$ .............................. C12Q 1/68; C12Q 1/00
(52) U.S. Cl. ................................. 435/6; 435/4
(58) Field of Search ....................... 435/4, 6; 536/23.1

(56) References Cited

U.S. PATENT DOCUMENTS

| | | |
|---|---|---|
| 5,484,707 A | 1/1996 | Goldblum et al. |
| 6,093,723 A | 7/2000 | Miao et al. |
| 6,096,556 A | 8/2000 | Heinecke |
| 6,113,324 A | 9/2000 | Huber |
| 6,113,898 A | 9/2000 | Anderson et al. |
| 6,200,978 B1 | 3/2001 | Maw et al. |

OTHER PUBLICATIONS

Burney et al., "The chemistry of DNA damage from nitric oxide and peroxynitrite", *Mutation Res.*, 424:37–49, 1999.
Burney, S. et al., "DNA damage in deoxynucleosides and oligonucleotides treated with peroxynitrite", *Chem. Res. Toxicol.*, 12:513–520, 1999.
Byun J. et al., "8–Nitro–2'deoxyguanosine, a specific marker of oxidation by reactive nitrogen species, is generated by the myeloperoxidase–hydrogen peroxide–nitrite system of activated human phagocytes", *Biochemistry*, 38:2590–2600, 1999.
Chwang, T.Ling et al., "Synthesis of nucleoside nitrates", *J. Carbohydrates Nucleosides Nucleotides*, 7(6):405–431, 1980.
Diplock et al., "Functional food science and defence against reactive oxidative species", *Brit. J. Nutrition* 80 (Supp. 1):S77–S112, 1998.
Douki, Thierry et al., "An adduct between peroxynitrite and 2'-deoxyguanosine: 4,5-dihydro-5-hydroxy-4-(nitroxooxy)-2'-deoxyguanosine", *Chem. Res. Toxicol.*, 9:3–7, 1996.
Fukuyama et al., "Clinical evidence of peroxynitrite formation in chronic renal failure patients with septic shock", *Free Radical Biol. & Med.* 22:771–774, 1997.
Holwitt, Joel, "The effect of peroxynitrite on DNA synthesis of 8–nitroguanine and a physical chemical study", Presented to the Intel International Science and Engineering Fair, May 5, 1999.
Holwitt, Gregory, "The synthesis and detection of 8–nitroguanine in DNA", Presented to the Intel International Science and Engineering Fair, May 10, 2000.
Huang, Guang–Fu and Torrence, Paul F., "Nitration of pyrimidine bases and nucleotides by nitronium tetrafluoroborate, synthesis of 5–nitro–2'–deoxyuridine", *Journal of Organic Chemistry*, 42(24)3821:3824, 1977.
Hughes, "Relationships between nitric oxide, nitroxyl ion, nitrosonium cation and peroxynitrite,"*Biochim. Biophys. Acta* 1411:263–272, 1999.
Hurst and Lymar, "Toxicity of peroxynitrite and related reactive nitrogen species towards *Escherichia coli*," *Chem. Res. Toxicol.* 10:802–810, 1997.
Jayasena, S. D., "Aptamers: An Emerging Class of Molecules That Rival Antibodies in Diagnostic", *Clin. Chem.* 45: 1628–1650, 1999.
Lin, Weiei et al., "Study on DNA strand breaks induced by sodium nitroprusside, a nitric oxide donor, in vivo and in vitro", *Mut. Research*, 466:187–195, 2000.
Love, "Oxidative stress in neurological disease," *Brain Pathol.* 9:119–131, 1999.
Oikawa, Shinji and Kawanishi, Shosuke, "Site specific DNA damage at GGG sequence by oxidative stress may accelerate telomere shortening", *FEBS Letters* 453:365–368, 1999.
Routledge, Michael N., "Mutations induced by reactive nitrogen oxide species in the supF forward mutation assay", *Mutation Research* 450, 95–105, 450.
Schwemmer, M., et al., "How urine analysis reflects oxidative stress—nitrotyrosine as a potential marker", *Clin. Chim. Acta* 297:207–216, 2000.

(List continued on next page.)

Primary Examiner—Jean C. Witz
Assistant Examiner—Brett Ozga
(74) *Attorney, Agent, or Firm*—Blakely, Sokoloff, Taylor & Zafman

(57) ABSTRACT

Novel methods for the synthesis of 8-nitroguanine are provided. Compositions comprising 8-nitroguanine, made by the novel synthetic methods are also provided herein. Methods of use of 8-nitroguanine, made by the novel synthetic methods, as a standard for detection of 8-nitroguanine in samples are also encompassed within the scope of the present invention. The present invention further concerns methods of predicting organ transplant rejection and detecting exposure to environmental stressors, such as ionizing radiation, toxic chemicals or infectious agents, by detecting 8-nitroguanine in one or more samples from a transplant recipient or an organism exposed to stress.

5 Claims, 11 Drawing Sheets

OTHER PUBLICATIONS

Spencer J.P.E., et al., "Base Modification and Strand Breakage in Isolated Calf Thymus DNA and in DNA from Human Skin Epidermal Keratinocytes Exposed to Peroxynitrite of 3–Morpholinosydnonimine," *Chemical Research in Toxicology*, 9 (1996), p1 152–1158.

Tretyakova et al., "Peroxynitrite–induced DNA damage in the supF gene: correlation with the mutational spectrum," *Mutation Res.* 447:287–303, 2000.

Tuo et al., "Importance of guanine nitration and hydroxylation in DNA in vitro and in vivo," *Free Radical Biol. & Med.* 29:147–155, 2000.

Yermilov, V., et al., "Formation of 8–nitroguanine in DNA treated with peroxynitrite in vitro and its rapid removal from DNA by depurination." *FEBS Letters*, 376:207–210, 1995a.

Yermilov, V., et al., "Formation of 8–nitroguanine by the reaction of Guanine with peroxynitrite in vitro," *Carcinogenesis* 16:2045–2050, 1995b.

Yermilov, V. et al., "Effects of carbon dioxide–bicarbonate on induction of DNA single–strand breaks and formation of 8–nitroguanine, 8–oxoguanine and base–propenal mediated by peroxyn it rite," *FEBS Letters*, 399:67–70, 1996.

β-ELIMINATION

SINGLE STRAND BREAK IN DNA

COMPOSITIONS AND METHODS OF USE OF 8-NITROGUANINE

This application claims the benefit under 35 U.S.C. §119(e) of provisional U.S. patent application Ser. No. 60/203,062, filed on May 9, 2000.

This invention was made with Federal Government support under contract F41624-00-D-7000 awarded by the Department of the Air Force. The Government has certain rights in the invention.

BACKGROUND OF THE INVENTION

1. Field of the Invention

The present invention relates to the field of surrogate markers for the detection of stress in an organism. More specifically, the present invention relates to methods of use of 8-nitroguanine to detect stress in an organism, particularly as an early predictor of organ rejection in a transplant recipient. The present invention further relates to novel methods of synthesis of 8-nitroguanine and compositions comprising 8-nitroguanine.

2. Description of Related Art

Peroxynitrite is formed in the body by macrophages as part of the inflammation process (Yermilov et al., 1995a; Byun et al., 1999). Peroxynitrite can react with DNA to form 8-nitroguanine (Yermilov et al., 1995a, 1995b, 1996). It has been speculated that peroxynitrite may cause DNA or tissue damage, contributing to the multistage carcinogenesis process (Yermilov et al., 1995a; Douki et al., 1996; Spencer et al., 1996). Formation of 8-nitroguanine as a result of exposure to peroxynitrite could result in spontaneous depurination and single-stranded DNA breaks (Yermilov et al., 1995a), resulting in the release of 8-nitroguanine. Thus, 8-nitroguanine could potentially serve as a surrogate marker for stress in general and for inflammation-related stress in particular. More recently, it has been suggested that 8-nitroguanine does not spontaneously depurinate and that prior reports of spontaneous depurination were an artifact induced by non-physiological exposure to peroxynitrite (Tuo et al., 2000). The potential use of 8-nitroguanine as a surrogate marker for inflammation and stress, prior to the present invention, was thus uncertain.

Methods for non-invasive monitoring of stress, through the detection and quantification of 8-nitroguanine in body fluids such as blood, urine and sputum would be highly desirable. Such methods could provide, for example, a non-invasive method for predicting the likelihood of organ rejection in transplant recipients, or for detecting exposure to environmental stressors in the form of ionizing radiation, toxic chemicals or infectious agents like viruses and bacteria.

The development of such monitoring procedures would be facilitated by the availability of a low-cost method for production of 8-nitroguanine, which would be of use as a standard for calibration of monitoring systems. Present methods for the production of 8-nitroguanine are expensive and require the use of starting materials, such as 8-bromoguanine or peroxynitrite (Yermilov et al., 1995b; Spencer et al., 1996), that are highly toxic or that may not be readily available.

SUMMARY OF THE INVENTION

The present invention satisfies a long-standing need in the field, by providing a novel and low-cost method for production of 8-nitroguanine. In another embodiment, the present invention concerns methods for detecting and quantifying 8-nitroguanine in fluids, such as blood, urine or sputum. Further embodiments of the present invention concern compositions comprising 8-nitroguanine, made by the disclosed methods. Such compositions are of use as standards for calibrating equipment to detect 8-nitroguanine in samples.

In certain embodiments, the compositions and methods of the present invention are used for the detection and/or quantitation of exposure to environmental stressors such as ionizing radiation, toxic chemicals or infectious agents. In a preferred embodiment, the compositions and methods are of use for predicting the likelihood of organ rejection in transplant recipients. Such a non-invasive method for predicting the likelihood of organ rejection is superior to present methods that require biopsy samples from the transplanted organ.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
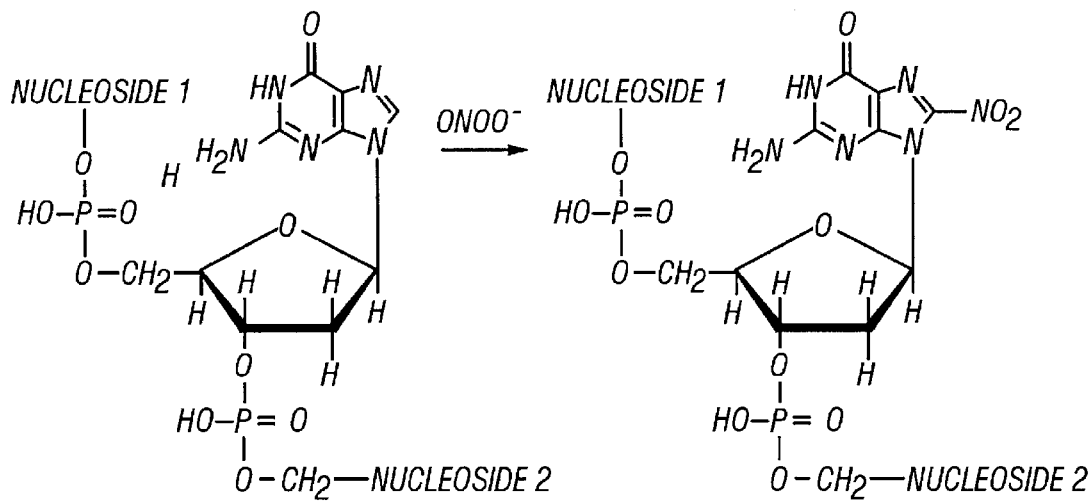
FIG. 1 illustrates the formation of 8-nitroguanine in DNA upon exposure to peroxynitrate and the β-elimination pathway for depurination and formation of single-stranded DNA breaks.
Figure 1:
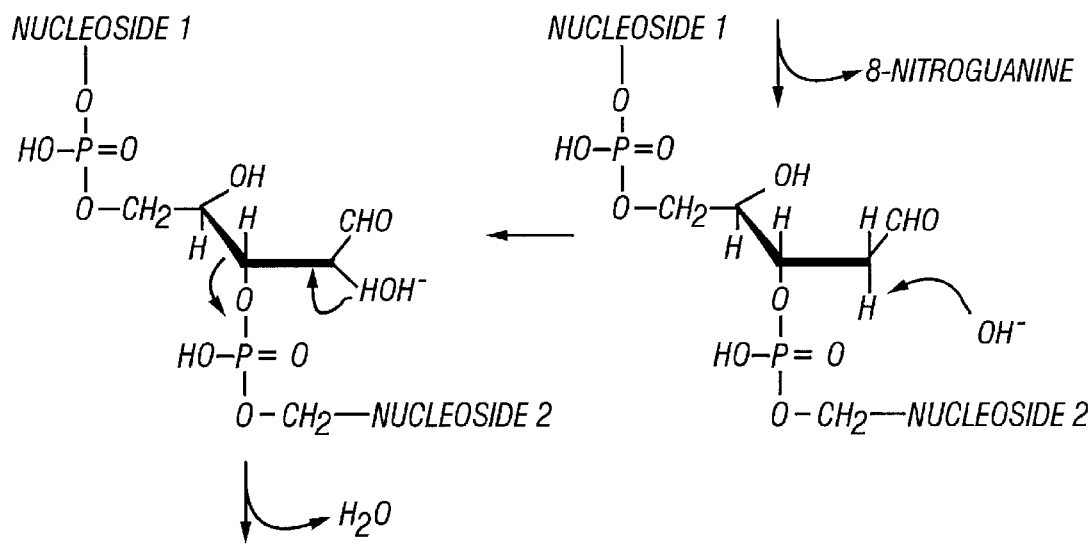
Figure 1:
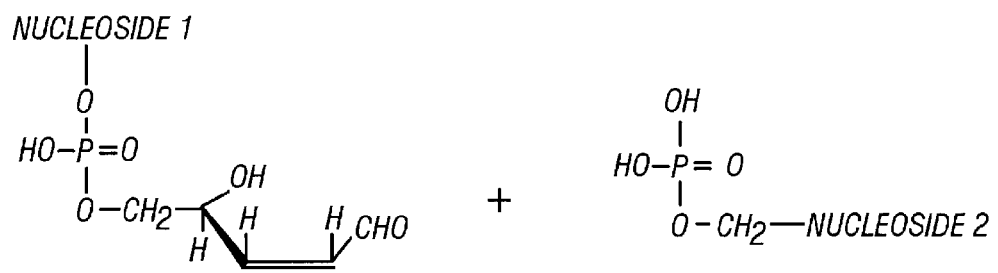

As used herein, the terms "a" and "an" mean one or more than one of an item.

As used herein to describe acid solutions, the term "concentrated" means that the solution comprises at least 10%, more preferably at least 20%, more preferably at least 30%, more preferably at least 40%, more preferably at least 50%, more preferably at least 60%, more preferably at least 70%, more preferably at least 80%, most preferably at least 90% by weight of the acid in the solution. Calculation of weight percent of acid solutions is well known in the art.

Methods for Low Cost Production of 8-Nitroguanine

The present invention discloses simple, efficient and low-cost methods for the production of 8-nitroguanine. The skilled artisan will realize that the methods disclosed are exemplary only. Modifications of the protocol contemplated within the scope of the invention include, but are not limited to, changes in reaction temperature, length of reaction time, pH of reaction, mixing conditions (e.g., stirring, refluxing, shaking), solvent, nitrating agent used and means of collecting 8-nitroguanine. Such modifications are a matter of routine experimentation for the skilled artisan, given the present disclosure and knowledge in the art of organic chemical synthesis.

The disclosed methods start with a suspension of guanine in an appropriate solvent. Exemplary solvents disclosed include acetonitrile, triflouoroacetic anhydride, water and dimethylformamide. However, other solvents of similar characteristics, for example nitromethane, are well known in the art and may be substituted within the scope of the invention.

The guanine is converted to 8-nitroguanine by addition of a nitrating agent. Exemplary nitrating agents disclosed herein include acetyl nitrate, nitronium tetrafluoroborate, trifluoroacetyl nitrate, nitric acid, and sodium nitrite. The skilled artisan will realize that alternative nitrating agents known in the art may be used in the practice of the invention. The only requirement is that the agent used must nitrate guanine to form 8-nitroguanine.

In certain embodiments, the 8-nitroguanine formed may be collected from the solvent by a variety of means known in the art. In preferred embodiments, 8-nitroguanine is present as part or all of a precipitate. The precipitate may be easily separated from the solvent by standard techniques. In certain preferred embodiments, the precipitate is collected by centrifugation, followed by removal of the liquid. The collected precipitate may be subject to one or more wash steps, followed by repeated centrifugation and drying. Other exemplary means of collection include filtration, allowing the precipitate to settle and decanting the liquid, or removing the liquid by lyophilization or drying. The only requirement of the collection step is that the 8-nitroguanine be separated from the bulk liquid component of the reaction mix. In certain embodiments where a dissolved form of 8-nitroguanine is desired, it is contemplated within the scope of the invention that collection of 8-nitroguanine may not be necessary.

Non-limiting methods for formation of 8-nitroguanine are disclosed in the Examples section below. The skilled artisan will realize that the scope of the present invention is not limited to the preferred embodiments disclosed in the Examples. The disclosed methods are superior to other methods for synthesis of 8-nitroguanine, for example by reaction of 8-bromoguanine with sodium nitrite (Tretyakova et al., 2000), or by reacting guanine with peroxynitrite (Yermilov et al., 1995b; Tuo et al., 2000). 8-Bromoguanine is expensive and not widely available, while peroxynitrite is highly toxic. The methods of the present invention use relatively inexpensive starting materials of comparatively low toxicity.

Separation and Quantitation of 8-Nitroguanine

It may be desirable to separate 8-nitroguanine from other sample constituents for the purposes of detection, quantitation, analysis or purification. The skilled artisan will realize that any methods known in the art for identification, purification or quantitation of small organic molecules like 8-nitroguanine may be used within the scope of the present invention. Examples of non-limiting techniques for 8-nitroguanine analysis would include mass spectrometry, high performance liquid chromatography (HPLC), gas chromatography, UV/VIS spectroscopy, electrochemical detection and capillary electrophoresis (Yermilov et al., 1995a, 1995b, 1996; Douki et al., 1996; Spencer et al., 1996; Diplock et al., 1998; Byun et al., 1999; Tretyakova et al., 2000; Tuo et al., 2000). In a preferred embodiment, 8-nitroguanine can be detected and quantified using aptamers (e.g., Jayasena, 1999) that bind specifically to 8-nitroguanine. The techniques discussed below are for exemplary purposes only and are not meant to limit the scope of the invention to the disclosed methods.

For analysis of 8-nitroguanine from biological samples, it may be desirable to pre-treat the sample to remove various components (whole cells, cell fragments, macromolecules, salts, precipitates) that could interfere with the analysis. Such methods are well known in the art and can include sample homogenization, enzymatic digestion, detergent or solvent extraction, centrifugation, filtration or precipitation. For analysis of urine samples, various contaminants may be precipitated out before analysis by acidification of the sample.

HPLC

High Performance Liquid Chromatography (HPLC) is characterized by a very rapid separation with high resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Separation of 8-nitroguanine by HPLC is well known in the art. For example, reverse-phase HPLC purification of 8-nitroguanine has been used by Douki et al. (1996), Spencer et al. (1996) and Byun et al. (1999). Reverse-phase HPLC of 8-nitroguanine that had been reduced to 8-aminoguanine was disclosed by Yermilov et al. (1996). Further non-limiting examples of HPLC analysis of 8-nitroguanine are disclosed below in the Examples section. A preferred method of detection of 8-nitroguanine with HPLC involves the use of an electrochemical detector associated with the HPLC system.

Mass Spectrometry

The basis of mass spectrometry is the identification of compounds by determination of their molecular mass. An exemplary method for detection of 8-nitroguanine by mass spectrometry was disclosed by Tretyakova et al. (2000), using negative-ion electrospray mass spectrometry. Other exemplary methods of detection using mass spectrometry and gas chromatography were disclosed in Spencer et al. (1996) and Byun et al. (1999). Tuo et al. (2000) disclosed a method of detection using HPLC with tandem mass spectrometry.

Microfluidic Techniques

Microfluidic techniques include separation on a platform such as microcapillaries, designed by ACLARA BioSciences Inc., or the LabChip™ liquid integrated circuits made by Caliper Technologies Inc. These microfluidic platforms require only nanoliter volumes of sample, in contrast to the microliter volumes required by other separation technologies. Miniaturizing some of the processes involved in genetic analysis has been achieved using microfluidic devices. For example, published PCT Application No. WO 94/05414, U.S. Pat. Nos. 5,304,487, 5,296,375 and 5,856,174 each of which is incorporated herein by reference.

Capillary Electrophoresis

In some embodiments microcapillary arrays are contemplated to be used for the analysis of 8-nitroguanine. Microcapillary array electrophoresis generally involves the use of a thin capillary or channel that may or may not be filled with a particular separation medium. Electrophoresis of a sample through the capillary provides a size based separation profile for the sample. The use of microcapillary electrophoresis has been reported in, e.g., Woolley and Mathies (1994). Microcapillary array electrophoresis generally provides a rapid method for size-based analysis of molecules. The high surface to volume ratio of these capillaries allows for the application of higher electric fields across the capillary without substantial thermal variation across the capillary, consequently allowing for more rapid separations. Microfabrication of microfluidic devices including microcapillary electrophoretic devices has been discussed in detail (e.g., Jacobsen et al., 1994; Effenhauser et al., 1994; Harrison et al., 1993; Effenhauser et al., 1993; Manz et al., 1992; and U.S. Pat. No. 5,904,824, incorporated herein by reference. Typically, these methods comprise photolithographic etching of micron scale channels on silica, silicon or other crystalline substrates or chips, and can be readily adapted for use in the present invention. In some embodiments, the capillary arrays may be fabricated from the same polymeric materials described for the fabrication of the body of the device, using injection molding techniques.

Tsuda et al., 1990, describes rectangular capillaries, an alternative to the cylindrical capillary glass tubes. Some advantages of these systems are their efficient heat dissipation due to the large height-to-width ratio and, hence, their high surface-to-volume ratio and their high detection sensitivity for optical on-column detection modes. These flat separation channels have the ability to perform two-dimensional separations, with one force being applied across the separation channel, and with the sample zones detected by the use of a multi-channel array detector.

In many capillary electrophoresis methods, the capillaries, e.g., fused silica capillaries or channels etched, machined or molded into planar substrates, are filled with an appropriate separation/sieving matrix. Typically, a variety of sieving matrices are known in the art may be used in the microcapillary arrays. Examples of such matrices include, e.g., hydroxyethyl cellulose, polyacrylamide, agarose and the like. Generally, the specific gel matrix, running buffers and running conditions are selected to maximize the separation characteristics of the particular application. For example, running buffers may include denaturants, chaotropic agents such as urea or the like, to denature nucleic acids in the sample.

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography (Freifelder, 1982).

Aptamers

In certain preferred embodiments, the identification and quantitation of 8-nitroguanine may be accomplished using one or more aptamers that specifically bind to 8-nitroguanine. The term "aptamer" refers to an oligonucleotide that is capable of forming a complex with an intended target substance ("analyte"), such as 8-nitroguanine. The binding is target-specific in the sense that other materials which may accompany the target do not bind to the aptamer. "Target-specific" means that the aptamer binds to target analyte with a much higher degree of affinity than it binds to contaminating materials. The meaning of specificity in this context is thus similar to the meaning of specificity as applied to antibodies, for example.

Methods of constructing and determining the binding characteristics of aptamers are well known in the art. For example, such techniques are described in Lorsch and Szostak (1996) and in U.S. Pat. Nos. 5,582,981, 5,595,877 and 5,637,459, each incorporated herein by reference.

Aptamers may be prepared by any known method, including synthetic, recombinant, and purification methods, and may be used alone or in combination with other aptamers specific for the same target. Further, the term "aptamer" specifically includes "secondary aptamers" containing a consensus sequence derived from comparing two or more known aptamers that bind to a given target.

As used in this section of the specification, "binding" refers to an interaction or binding between a target and an oligonucleotide or aptamer, resulting in a sufficiently stable complex so as to permit separation of oligonucleotide:target complexes from uncomplexed oligonucleotides under given binding or reaction conditions. Binding is mediated through hydrogen bonding or other molecular forces.

In general, a minimum of approximately 3 nucleotides, preferably at least 5 nucleotides, are necessary to effect specific binding. The only apparent limitations on the binding specificity of the target/oligonucleotide complexes of the invention concern sufficient sequence to be distinctive in the binding oligonucleotide and sufficient binding capacity of the target substance to obtain the necessary interaction. Oligonucleotides of sequences shorter than 10 bases may be feasible if the appropriate interaction can be obtained in the context of the environment in which the target is placed, although aptamers of about 10, 15, 20, 25, 30, 35, 40, 45, 50, 55, 60, 65, 70, 75, 80, 85, 90, 95 or 100 nucleotides or more in length are contemplated within the scope of the present invention. Although in preferred embodiments the oligonucleotides are single-stranded or double-stranded, it is contemplated that aptamers may sometimes assume triple-stranded or quadruple-stranded structures.

The specifically binding oligonucleotides need to contain the sequence that confers binding specificity, but may be extended with flanking regions and otherwise derivatized. In preferred embodiments of the invention, aptamer binding sites will be flanked by known, amplifiable sequences, facilitating the amplification of the nucleic acids by PCR or other amplification techniques. In a further embodiment, the flanking sequence may comprise a specific sequence that preferentially recognizes or binds a moiety to enhance the immobilization of the aptamer to a substrate.

The aptamers found to bind to the targets may be isolated, sequenced, and/or amplified or synthesized as conventional DNA or RNA molecules. Alternatively, aptamers of interest may comprise modified oligomers. Any of the hydroxyl groups ordinarily present in nucleic acids may be replaced by phosphonate groups, phosphate groups, protected by a standard protecting group, or activated to prepare additional linkages to other nucleotides, or may be conjugated to solid supports. The 5' terminal OH is conventionally free but may be phosphorylated. Hydroxyl group substituents at the 3' terminus may also be phosphorylated. The hydroxyls may be derivatized by standard protecting groups. One or more phosphodiester linkages may be replaced by alternative linking groups. These alternative linking groups include, exemplary embodiments wherein P(O)O is replaced by P(O)S, P(O)NR$_2$, P(O)R, P(O)OR', CO, or CNR$_2$, wherein R is H or alkyl (1–20C) and R' is alkyl (1–20C); in addition, this group may be attached to adjacent nucleotides through O or S. Not all linkages in an oligomer need to be identical.

The oligonucleotides used as starting materials in the process of the invention to determine 8-nitroguanine specific binding sequences may be single-stranded or double-stranded DNA or RNA. In a preferred embodiment, the sequences are single-stranded DNA. The use of DNA eliminates the need for conversion of RNA aptamers to DNA by reverse transcriptase prior to PCR amplification. Furthermore, DNA is less susceptible to nuclease degradation than RNA. In preferred embodiments, the starting nucleic acid will contain a randomized sequence portion, generally including from about 10 to 400 nucleotides, more preferably 20 to 100 nucleotides. The randomized sequence is flanked by primer sequences that permit the amplification of nucleic acids found to bind to the 8-nitroguanine. The flanking sequences may also contain other convenient features, such as restriction sites. These primer hybridization regions generally contain 10 to 30, more preferably 15 to 25, and most preferably 18 to 20, bases of known sequence.

Both the randomized portion and the primer hybridization regions of the initial oligomer population are preferably constructed using conventional solid phase techniques. Such techniques are well known in the art, such methods being described, for example, in Froehler, et al., (1986a, 1986b, 1988, 1987). Oligonucleotides may also be synthesized using solution phase methods such as triester synthesis, known in the art. For synthesis of the randomized regions, mixtures of nucleotides at the positions where randomization is desired are added during synthesis.

Any degree of randomization may be employed. Some positions may be randomized by mixtures of only two or three bases rather than the conventional four. Randomized positions may alternate with those that have been specified. Indeed, it is helpful if some portions of the candidate randomized sequence are in fact known.

SELEX Technology

A preferred method of selecting for 8-nitroguanine specific aptamers involves the SELEX process. The SELEX process is described in U.S. Pat. Nos. 5,475,096, and 5,270,163, (see also WO91/19813), each specifically incorporated by reference.

The SELEX method involves selection from a mixture of candidate oligonucleotides and step-wise iterations of binding, partitioning and amplification, using the same general selection scheme, to achieve virtually any desired criterion of binding affinity and selectivity. Starting from a mixture of nucleic acids, preferably comprising a segment of randomized sequence, the method includes the following steps. Contacting the mixture with the target under conditions favorable for binding. Partitioning unbound nucleic acids from those nucleic acids that have bound specifically to target analyte. Dissociating the nucleic acid-analyte complexes. Amplifying the nucleic acids dissociated from the nucleic acid-analyte complexes to yield mixture of nucleic acids that preferentially bind to the analyte. Reiterating the steps of binding, partitioning, dissociating and amplifying through as many cycles as desired to yield highly specific, nucleic acids that bind with high affinity to the target analyte.

In the SELEX process, a candidate mixture of nucleic acids of differing sequence is prepared. The candidate mixture generally includes regions of fixed sequences (i.e., each of the nucleic acids contains the same sequences) and regions of randomized sequences. The fixed sequence regions are selected to: (a) assist in the amplification steps; (b) mimic a sequence known to bind to the 8-nitroguanine; or (c) promote the formation of a given structural arrangement of the nucleic acids. The randomized sequences may be totally randomized (i.e., the probability of finding a given base at any position being one in four) or only partially randomized (i.e., the probability of finding a given base at any location can be any level between 0 and 100 percent).

The candidate mixture is contacted with the 8-nitroguanine under conditions favorable for binding of 8-nitroguanine to nucleic acid. The interaction between the 8-nitroguanine and the nucleic acids can be considered as forming nucleic acid-8-nitroguanine pairs with those nucleic acids having the highest affinity for the 8-nitroguanine.

The nucleic acids with the highest affinity for the 8-nitroguanine are partitioned from those nucleic acids with lesser affinity. Because only a small number of sequences (possibly only one molecule of nucleic acid) corresponding to the highest affinity nucleic acids exist in the mixture, it is generally desirable to set the partitioning criteria so that a significant amount of nucleic acids in the mixture (approximately 5–50%) are retained during partitioning.

Those nucleic acids selected during partitioning as having higher affinity for the 8-nitroguanine are amplified to create a new candidate mixture that is enriched in higher affinity nucleic acids.

By repeating the partitioning and amplifying steps, each round of candidate mixture contains fewer and fewer weakly binding sequences. The average degree of affinity of the nucleic acids to the 8-nitroguanine will generally increase with each cycle. The SELEX process can ultimately yield a mixture containing one or a small number of nucleic acids having the highest affinity for 8-nitroguanine.

In preferred embodiments, the binding interaction between 8-nitroguanine and one or more selected aptamers is highly specific. The binding interaction between 8-nitroguanine and high specificity aptamers will necessarily involve more than the standard Watson-Crick hydrogen bond formation observed between guanine and cytosine residues in vivo. It is expected that 8-nitroguanine will form hydrogen bonds with any oligonucleotides containing a cytosine residue. However, such aptamers will also bind to guanine and other guanine derivatives besides 8-nitroguanine. In the most preferred embodiments, the high specificity aptamer binds selectively to 8-nitroguanine in preference to guanine and other guanine derivatives. The skilled artisan can readily determine the relative binding affinity of an aptamer for 8-nitroguanine compared to guanine or other guanine derivatives. For example, 8-nitroguanine may be attached to a solid support, preferably through the use of a linker moiety. A candidate mixture of nucleic acids may be exposed to the attached 8-nitroguanine and allowed to bind. After washing, the aptamers bound to 8-nitroguanine may be exposed to a solution containing guanine. Those aptamers that are competitively released from 8-nitroguanine by soluble guanine will be less preferred for use in detection of 8-nitroguanine, as they will also react with guanine.

Aptamers produced for SELEX may be generated on a commercially available DNA synthesizer. The random region is produced by mixing equimolar amounts of each nitrogenous base (A,C,G, and T) at each position to create a large number of permutations (i.e., $4^n$, where "n" is the oligo chain length) in a very short segment. Thus a randomized 40 mer (40 bases long) would consist of $4^{30}$ or maximally $10^{24}$ different oligonucleotides. This provides dramatically more possibilities to find high affinity aptamers when compared to the $10^9$ to $10^{11}$ variants of murine antibodies produced by a single mouse. The random region is flanked by two short Polymerase Chain Reaction (PCR) primer regions to enable amplification of the small subset of oligonucleotide aptamers that bind tightly to the target analyte.

Many RNA oligonucleotides have performed well due to their propensity to form secondary and tertiary structure "binding pockets", but RNAses abound in nature making RNA oligonucleotides less desirable for use. Fortunately, many single and double stranded SELEX DNA aptamers have also demonstrated specificity and high affinity binding to their intended targets.

Nucleic Acid Chips and Aptamer Arrays

Nucleic acid chips and aptamer array technology provide a means of rapidly screening analytes for their ability to hybridize to a potentially large number of single stranded nucleic acid probes immobilized on a solid substrate. In preferred embodiments, the nucleic acids are DNA. Specifically contemplated are chip-based DNA technologies such as those described by Hacia et al., 1996 and Shoemaker et al., 1996. These techniques involve quantitative methods for analyzing large numbers of samples rapidly and accurately. The technology capitalizes on the binding properties of single stranded DNA to screen samples. (Pease et al., 1994; Fodor et al., 1993; Southern et al., 1994; Travis, 1997; Lipshutz et al., 1995; Matson et al., 1995; each of which is incorporated herein by reference.)

A nucleic acid chip or aptamer array consists of a solid substrate upon which an array of single stranded nucleic acid molecules have been attached. For screening, the chip or array is contacted with a sample containing analyte which is allowed to bind. The degree of stringency of binding may be manipulated as desired by varying, for example, salt concentration, temperature, pH and detergent content of the medium. The chip or array is then scanned to determine which nucleic acids have bound to the analyte. Prior to the present invention, DNA chips were typically used to bind to target DNA or RNA molecules in a sample.

A variety of DNA chip formats are described in the art, for example U.S. Pat. Nos. 5,861,242 and 5,578,832 which are expressly incorporated herein by reference. The structure of a nucleic acid chip or array comprises: (1) an excitation source; (2) an array of probes; (3) a sampling element; (4) a detector and (5) a signal amplification/treatment system. A chip may also include a support for immobilizing the probe.

In particular embodiments, an aptamer may be tagged or labeled with a substance that emits a detectable signal. The tagged or labeled species may be fluorescent, phosphorescent, or luminescent, or it may emit Raman energy or it may absorb energy. When the aptamer binds to a targeted analyte, such as 8-nitroguanine, a signal is generated that is detected by the chip. The signal may then be processed in several ways, depending on the nature of the signal.

The aptamer may be immobilized onto an integrated microchip that also supports a phototransducer and related detection circuitry. Alternatively, an aptamer may be immobilized onto a membrane or filter which is then attached to the microchip or to the detector surface itself.

The aptamers may be directly or indirectly immobilized onto a transducer detection surface to ensure optimal contact and maximum detection. The ability to directly synthesize on or attach polynucleotide probes to solid substrates is well known in the art. See U.S. Pat. Nos. 5,837,832 and 5,837,860 both of which are expressly incorporated by reference. A variety of methods have been utilized to either permanently or removably attach the nucleic acids to the substrate. Exemplary methods are described above under the section on immobilization. When immobilized onto a substrate, the aptamers are stabilized and may be used repeatedly.

Within the scope of the present invention, aptamers specific for 8-nitroguanine could be incorporated into an aptamer array designed to rapidly screen samples, such as blood, sputum or urine, for the presence of various compounds of interest, including 8-nitroguanine.

Prediction of Organ Rejection or Detection of Exposure to Environmental Stressors 8-Nitroguanine may be used as a surrogate marker for predicting the likelihood of rejection in an organ transplant recipient. In preferred embodiments, samples obtained from a transplant recipient by non-invasive means, such as blood or urine samples, are analyzed for 8-nitroguanine by the methods of the present invention. Detection of 8-nitroguanine in greater than baseline levels from a blood or urine sample of a transplant recipient is predictive of organ rejection. Such patients should be closely monitored and subjected to an appropriate treatment regimen, such as antibiotic, immunosuppressant or other therapy. Methods for prediction and treatment of organ transplant rejection are discussed in U.S. Pat. Nos. 5,484,707, 6,093,723, 6,113,898, 6,133,324 and 6,200,978, each incorporated herein by reference in its entirety. A particularly high likelihood of organ rejection is indicated by a large spike or sustained elevated level of 8-nitroguanine in the blood or urine. Individuals showing such symptoms should be aggressively treated to reduce the risk of organ rejection.

The term "baseline levels" means levels of 8-nitroguanine that would normally be found in individuals who have not been exposed to environmental stressors or who are not at risk for organ rejection. The determination of baseline levels of 8-nitroguanine is well within the skill in the art. The skilled artisan will realize that alternative methods for determination of baseline levels may be employed depending on the target population and the condition to be detected. In the case of organ transplant recipients, an exemplary procedure would be to measure levels of 8-nitroguanine in the patient before and after transplantation, with monitoring preferable on at least a daily basis following transplantation. After the patient has stabilized, monitoring may occur at longer intervals of weekly, later monthly duration. The frequency of monitoring will be determined by the physician's evaluation of the patient's stability. The initial determination of "baseline levels" will be based on the levels of 8-nitroguanine observed in the patient preceding transplant. After the patient has stabilized following organ transplant, a new "baseline level" may be determined from the levels of 8-nitroguanine observed in the stabilized patient.

Alternative methods of determining "baseline levels" are available. Levels of 8-nitroguanine may be determined in a cohort of organ transplant recipients before and after transplantation. The cohort may be monitored for 8-nitroguanine levels following transplantation and the information correlated with their transplant status. Individuals who experience transplant rejection are informative for the levels of 8-nitroguanine that are predictive of transplant rejection. The levels of 8-nitroguanine observed in such individuals preceding transplant rejection can be determined. This information can be used to construct a more defined "baseline level" of 8-nitroguanine and to establish 8-nitroguanine cutoff levels where more extensive monitoring and aggressive therapy are appropriate.

In the context of determining exposure to environmental stressors, a cohort of individuals who have not been exposed to environmental stressors may be selected and the levels of 8-nitroguanine in their blood or urine determined. From this data, the range, mean and standard deviation of 8-nitroguanine levels in control normal individuals may be determined. This in turn may be used to define the "baseline levels" of 8-nitroguanine for exposure to environmental stress.

Additional cohorts of individuals with known exposure to identified levels of an environmental stressor, such as toxic chemicals, ionizing radiation or infectious agents may also be selected. Levels of 8-nitroguanine in such individuals may be readily determined by the methods disclosed herein. This information may be used to construct tables correlating the level of exposure to an environmental stressor with the levels of 8-nitroguanine found in the individual. Such data may also take into account the length of time following exposure that samples are taken for determination of 8-nitroguanine. The effects of chronic versus acute exposure to an environmental stressor on 8-nitroguanine levels may also be readily determined by the skilled artisan.

The skilled artisan will realize that 8-nitroguanine may be used within the scope of the present invention as an indicator of exposure to environmental stressors, such as ionizing radiation, toxic chemicals or infectious agents. An acute exposure to such a stressor will result in a pike in 8-nitroguanine in the blood or urine of an individual, while chronic exposure will result in long-term elevation of 8-nitroguanine levels. The levels of 8-nitroguanine detected are indicative of the degree of exposure, with higher exposure resulting in higher levels of 8-nitroguanine.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Exposure of DNA to Peroxynitrite Results in Formation of 8-Nitroguanine, Followed by Depurination and Production of Single-Stranded DNA Breaks Peroxynitrite can be formed in vivo by the reaction of nitric oxide (NO) with superoxide anion (Fukuyama et al., 1997; Hurst and Lymar, 1997; Burney et al., 1999; Hughes, 1999; Love, 1999; Schwemmer et al., 2000). This extremely rapid reaction occurs in macrophages during the inflammation process. While the peroxide anion is stable, the acid form, peroxynitrous acid (pKa=6.8) is very unstable, with a half life of 1.9 seconds at pH 7.4. Peroxynitrite may be synthesized in vitro by, for example, reaction of potassium or sodium nitrite with hydrogen peroxide in acid, then immediate stabilization of the peroxynitrite formed by addition of base such as NaOH.

The reaction between nitrite and hydrogen peroxide to form peroxynitrite is acid catalyzed, but so is the decomposition of peroxynitrite. When nitrite and hydrogen peroxide were mixed in the presence of acid, a bright yellow compound formed. Addition of base upon formation of the bright yellow color stopped both the synthetic reaction and the breakdown reaction. The final concentration of peroxynitrite varied depending on the timing of additions. Concentrations of peroxynitrite achieved by this method, measured by a molar extinction coefficient of $1.67 \times 10^3$ per mole per liter at 302 nm, varied from 90 to 134 mM.

Products reported to be formed by the attack of reactive oxygen species, such as peroxynitrite, with guanine or deoxyguanosine include xanthine, 8-hydroxyguanine, 8-hydroxy-deoxyguanosine, 8-oxoguanine, 7-methyl-8-hydroxyguanine, 7-hydro-8oxo-2'-deoxyguanosine, 8-oxo-7,8-dihydro-2'-deoxyguanine, 4,5-dihydro-5-hydroxy-4-(nitrosooxy)-2'-deoxyguanosine and 8-nitroguanine (Yermilov et al., 1996; Diplock et al., 1998; Burney et al., 1999; Love, 1999; Tuo et al., 2000). It has been suggested that 8-nitroguanine could be used as a marker for DNA damage induced by peroxynitrite in inflamed tissues (Yermilov et al., 1995a, 1996; Byun et al., 1999). Conversely, other reports have suggested that 8-nitroguanine is not formed in vivo by spontaneous depurination of oxidatively damaged DNA (Tuo et al., 2000).

The present results confirm that exposure of DNA to peroxynitrite results in formation of 8-nitroguanine, followed by depurination and formation of single-stranded DNA breaks, as indicated in FIG. 1. Single-stranded DNA breaks were detected by a decrease in the degree of supercoiling of plasmid DNA.

As the degree of DNA damage increases, the likelihood of two single stranded breaks occurring within a few bases on the opposite strands of double-stranded DNA also increases. Double-stranded DNA breaks result in a decrease in the length of the DNA molecule, detectable as a decreased viscosity of linear double-stranded DNA. This method was also used to assay for depurination and DNA strand breakage.

Plasmid DNA Methods and Materials

*E coli* strain JM109 containing plasmid DNA (pUC19) was grown in 2 ml of M9 media to which 24 μl of 2.5 mg/ml ampicillin was added. Following incubation for approximately 8 hours, the culture was transferred to 50 ml of M9 media containing ampicillin. The following day, 25 ml of the overnight culture was used to inoculate 500 ml of M9 media containing ampicillin. When the optical density at 600 nm of the bacterial culture reached between 0.6 and 0.8 O.D., 50 mg of chloramphenicol, dissolved in 1 ml of absolute ethanol, was added to the culture and the culture was incubated overnight.

The next morning, cells were harvested by centrifugation. Plasmid DNA was isolated using a Promega Wizard Max-iPrep Kit. Cells were resuspended in resuspension solution, and lysis buffer was added. The buffer was neutralized after 20 min, the solution was centrifuged and the supernatant collected. To the supernatant was added 0.5 volumes of isopropanol, which caused the DNA to precipitate. The DNA was collected by centrifuged and resuspended in 2 ml of TAE buffer. Wizard MaxiPrep Resin DNA was then added to the DNA suspension to adsorb the DNA, and the resin transferred to a spin column. The resin was washed and the DNA was eluted from the column with TAE buffer by centrifugation. After removing the fine particles the DNA was ready for use. Its concentration was measured by absorbance at 260 nm (0.2 OD units=10 $\mu$g/ml).

Plasmid DNA was analyzed by electrophoresis in TAE buffer using a 1% agarose gel. Gels were run at a constant 100 volts using bromophenol blue as the tracking dye. Ethidium bromide was added to the gel to visualize the DNA. After an appropriate time, the DNA was visualized by illumination at 302 nm. Polaroid photographs were taken, and later digitized for densitometric analysis.

The Effect of pH on Formation of Single-Stranded DNA Breaks

The effect of pH on the conversion of supercoils to open circles by peroxynitrite was examined. The pH range used was from 4 and 10. Buffers were prepared at 0.5 M strength to minimize pH changes caused by the NaOH in the peroxynitrite solution. Buffers used were citrate, cacodylate, borate, phosphate and Tris.

The final volume of each microcentrifuge tube was 40 $\mu$l. Each tube contained 5 $\mu$l of plasmid DNA and 34 $\mu$l of buffer at either pH 4, 5, 6, 7, 8, 9, or 10. Controls were run at pH 4, 7, and 10. One $\mu$l of peroxynitrite was added to each tube except controls, which received 1 $\mu$l of water. The DNA was incubated at room temperature for 30 minutes. DNA was analyzed as described above.

The effect of peroxynitrite concentration on the conversion of supercoils to open circles was determined at pH 5, 6, 7, 8, and 9. The final volume of each microcentrifuge tube was 50 $\mu$l Each tube contained 5 $\mu$l of plasmid DNA and 39 $\mu$l of 0.5 M buffer. Borate was used for the pH 7, 8 and 9 buffers, while cacodylate was used for the pH 5 and 6 buffers. One tube was given 1 $\mu$l of 1/20 stock concentration of peroxynitrite, other tubes were given either 1, 2, 4, or 6 $\mu$l of 1/10 stock concentration of peroxynitrite, and the remaining tubes were given 1, 2, 4, or 6 $\mu$l of the stock concentration for 9 different concentrations of peroxynitrite per experiment. A tenth tube acted as control with no peroxynitrite added. Water was added to bring volume up to 50 $\mu$l total volume. The DNA was incubated at room temperature for 30 minutes. DNA was analyzed as described above.

Viscosity Studies

Stock solutions of Sigma Calf Thymus DNA were made by dissolving DNA in 0.1 M $Na_2HPO_4$, pH 8, 0.1 M sodium cacodylate, pH 5, 0.1 M Tris, pH 8, and 0.1 M borate, pH 8. The final volume for all viscosity experiments was 40 ml and the DNA concentration was 420 $\mu$g/ml. Enough stock DNA was used to provide the final concentration required (usually 20 ml and the pH adjusted with either phosphoric acid or NaOH (except for pH 5 which used HCl). Peroxynitrite was added in 10 aliquots, and the pH maintained by the addition of phosphoric acid (except pH 5). For experiments using Tris or borate, HCl was used to maintain the pH. The volume was brought up to 40 ml by the addition of buffer. DNA was incubated at 37° C. Viscosities of the sample and control were taken at various times at 37° C. in a Stoney Brook Disposable Viscometer.

Preparation of Peroxynitrite

Peroxynitrite was synthesized by mixing ice cold solutions of 1.38 g $NaNO_2$ in 20 ml of water with 20 ml of water containing 2.27 g of 30% $H_2O_2$ and 0.33 ml concentrated $H_2SO_4$. Immediately 1.12 g NaOH in 20 ml of $H_2O$ (ice cold) was added. The reaction was performed on ice. Manganese dioxide was added to destroy unreacted hydrogen peroxide. The suspension was then filtered to collect the peroxynitrite. The concentration was determined using a molar extinction coefficient at 302 nm of $1.67 \times 10^3$ per mole per liter. Peroxynitrite was stored frozen at $-120°$ C.

Effect of Peroxynitrite on Supercoiled DNA

The conversion of supercoiled pUC19 plasmid DNA to open circles by peroxynitrite in vitro was examined. The effect of pH on the reaction of peroxynitrite with DNA, holding peroxynitrite concentration constant was examined. Then, holding pH constant, peroxynitrite concentration was varied. Finally, the effect of the buffer composition on the conversion of supercoils to open circles by peroxynitrite was examined.

Peroxynitrite was effective at converting supercoiled plasmid DNA to open circles at all pHs, even though peroxynitrite is unstable at acidic pHs. Even at the acidic pH, there was very little supercoiled DNA remaining after exposure to peroxynitrite. The lowest rate of supercoil reduction (a measure of single-stranded DNA breaks) occurred at pH 7. The amount of supercoiling remaining decreased as pH was increased from 7 to 10.

The effect of pH on the concentration dependence of peroxynitrite reduction of DNA supercoiling was observed. The concentration effect of peroxynitrite was similar at pH values ranging from 5 to 9, demonstrating that pH has little effect on the reaction between DNA and peroxynitrite.

The effect of pH on DNA supercoiling at constant peroxynitrite concentration was also observed. The maximum levels of remaining DNA supercoiling (indicative of the minimum levels of single-stranded DNA breaks) were observed between pH 7 and 8. A buffer effect was observed on single-strand nick formation, with lower levels of peroxynitrite induced nicks observed in Tris-phosphate buffer with EDTA, compared with borate buffer in the absence of EDTA. Under the conditions of this study, a minimum of about a 45% reduction in DNA supercoiling was observed following exposure to peroxynitrite.

Viscosity Data

The viscosity studies examined the effect of pH (at constant peroxynitrite concentration), the effect of increasing peroxynitrite concentration at constant pH, and the effect of buffer on viscosity. Data was collected using a falling needle viscometer. This type of viscometer generates a very low shear force and is suitable for use with non-Newtonian fluids, such as DNA solutions.

As peroxynitrite exposed DNA depurinates, single strand breaks accumulate. Eventually two single strand breaks on opposite strands may occur within a few nucleotides of each other. When this happens, a break in the double stranded DNA molecule results. This shortens the DNA molecule and reduces the viscosity of the solution. The data was recorded as the relative viscosity and specific viscosity of the solution.

Viscosity decreased with time of exposure to peroxynitrite at all pH values, decreasing within the first two hours of peroxynitrite exposure. This data agreed with the results on plasmid supercoiling. The decrease in viscosity was dependent on the concentration of peroxynitrite used. The effects of buffer composition on viscosity reduction were similar to those reported above for supercoiled DNA. The activation energy of the depurination reaction was determined by Arrhenius analysis. The calculated activation energy was 917 Joules/mole, showing a relatively low activation energy for formation of single-stranded DNA nicks by peroxynitrite.

These results demonstrate that exposure to peroxynitrite in vitro causes single-stranded and double-stranded breaks in DNA, consistent with the formation of 8-nitroguanine followed by spontaneous depurination of 8-nitroguanine.

Example 2

Novel Method for Synthesis of 8-Nitroguanine

There is currently no simple method for producing 8-nitroguanine. 8-Nitroguanine may be synthesized by reacting guanine with peroxynitrite (Yermilov et al., 1995b). However this synthesis produces products other than 8-nitroguanine and has relatively low efficiency, since a large amount of unreacted guanine remains. Further, as a suspected carcinogen and mutagen, peroxynitrite is difficult to work with. The method also requires an extensive workup, including repeated chromatography to purify 8-nitroguanine from the contaminants. An alternative method, reacting 8-bromoguanine with sodium nitrite (Tretyakova et al., 2000), requires the use of an expensive and not generally available starting material (8-bromoguanine).

An exemplary novel method for synthesis of 8-nitroguanine within the scope of the present invention makes use of acetic anhydride as a solvent and a reactant. By adding nitric acid to the acetic anhydride, acetyl nitrate is created as the nitrating agent. The nitric acid is added step wise to acetic anhydride solvent that already contains the guanine, providing a one-step reaction for production of 8-nitroguanine from guanine.

The product of this reaction was analyzed in comparison with data on the published spectra of 8-nitroguanine. The reaction product was reduced by zinc-HCl or sodium hydrosulfite. Under these conditions, 8-nitroguanine is reduced to form 8-aminoguanine. This reduced product was compared by HPLC and spectral analysis with 8-aminoguanine synthesized by acid hydrolysis of commercially available 8-aminoguanosine.

8-Nitroguanine Synthesis

The following methods are exemplary only and are not meant to be limiting to the scope of the present invention. The skilled artisan will realize that the materials and reaction conditions may be varied by routine experimentation to produce 8-nitroguanine. It is contemplated within the scope of the invention that a wide variety of materials and conditions may be used, so long as 8-nitroguanine is a primary product of the reaction. "Primary product" means that 8-nitroguanine forms at least 30 %, more preferably at least 40%, more preferably at least 50%, more preferably at least 60%, more preferably at least 70%, more preferably at least 80%, more preferably at least 90%, most preferably at least 95% of the products of the reaction.

Method 1

Suspend 1 g of guanine in 25 g of acetic anhydride. Add 0.303 ml of 90% HNO3. Leave overnight at room temperature with stirring. Collect yellow liquid by either vacuum filtration or centrifugation. Boil and then cool on ice. After a precipitate forms, collect by centrifugation. Lyophilize to dryness.

Method 2

Prepare peroxynitrite as discussed above. Add 50 mg of guanine and stir overnight at room temperature. Add acid to precipitate the reaction product. Collect the precipitate by centrifugation an lyophilize to dryness.

Method 3

Cool 0.438 ml of acetic anhydride on ice. Add 0.303 ml of 90% nitric acid to the acetic anhydride to form acetyl nitrate. To 25 ml of acetonitrile, add 0.5 g of guanine. Once the red color disappears from the acetyl nitrate, slowly add it to the guanine suspension and reflux for about 4 hours. Collect the precipitated reaction product by centrifugation. Wash twice with acetonitrile and dry overnight at room temperature.

Method 4

Suspend 0.5 g of guanine in 25 ml of acetonitrile. Add 0.439 g. of nitronium tetrafluoroborate and reflux for about 4 hours. After a precipitate forms, collect by centrifuging. Wash twice with acetonitrile, then wash with water to remove any remaining nitronium tetrafluoroborate. Lyophilize to dryness.

Method 5

Suspend 1.0 g of guanine in 8.4 ml of trifluoroacetic anhydride. Add 3 aliquots of 0.1 ml of 90% nitric acid and stir overnight at room temperature. Collect the precipitate by centrifuging. Wash the pellet twice with 0.5 M phosphate buffer, pH 7, and then wash with water to remove the buffer. Lyophilize to dryness.

Method 6

Suspend 0.1 g of 8-bromoguanine in 10 ml of either water or dimethylformamide. Add 0.1 g of sodium nitrite and reflux for about 4 hours. Collect the precipitate by centrifuging. Wash the pellet twice with water and then lyophilize to dryness.

HPLC Chromatography

In an exemplary embodiment, 8-nitroguanine may be analyzed by gradient reverse-phase HPLC using a Phenomenex C18 Aqua column (5 micron). The buffer system consisted of Buffer A (20 mM ammonium formate, pH 4, 1% methanol) and Buffer B (20 mM ammonium formate, pH 4, 40% methanol), using a gradient from 100% buffer A to 20% buffer A, 80% buffer B. The gradient may be run from about 25 to about 50 minutes.

Analysis of 8-Nitroguanine

All synthetic preparations were analyzed by HPLC, using a C18 column with isocratic 0.020 M ammonium formate, pH 4.0, 1% methanol at a flow rate of 2 ml/min. The eluate was monitored with a diode array detector at 254 nm. Since 8-nitroguanine is one of the products produced when peroxynitrite reacts with guanine, the retention times of the synthetic products were compared to the retention times of the peaks from the peroxynitrite treatment of DNA. The spectra of the products were also compared with the published spectra of 8-nitroguanine.

Characterization of Synthetic Products

Figure 2:
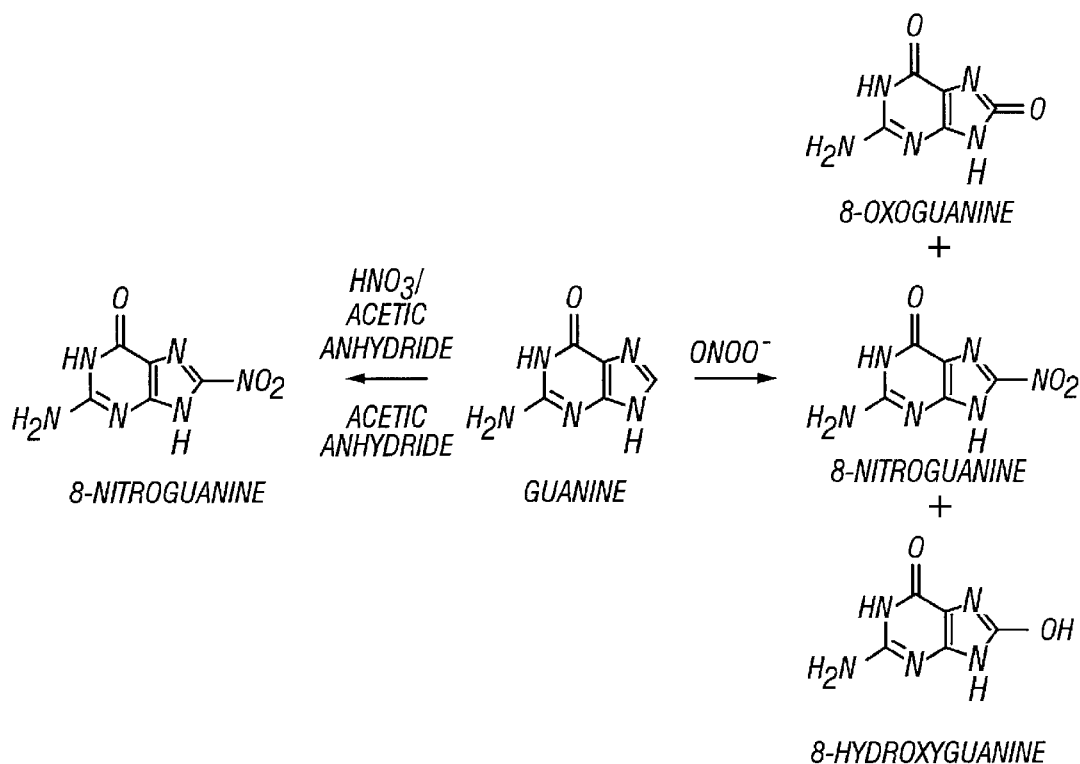
FIG. 2 illustrates alternative pathways for production of 8-nitroguanine.
Figure 3B:
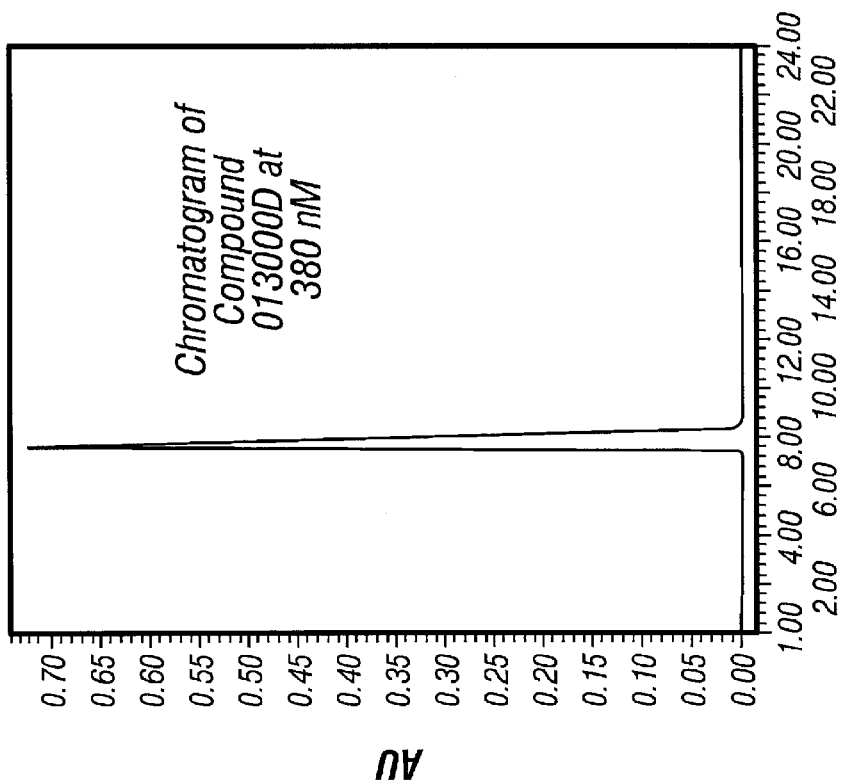
FIG. 3 illustrates the chromatography of 8-nitroguanine made by exposure of guanine to acetic anhydride and nitric acid.
Figure 3A:
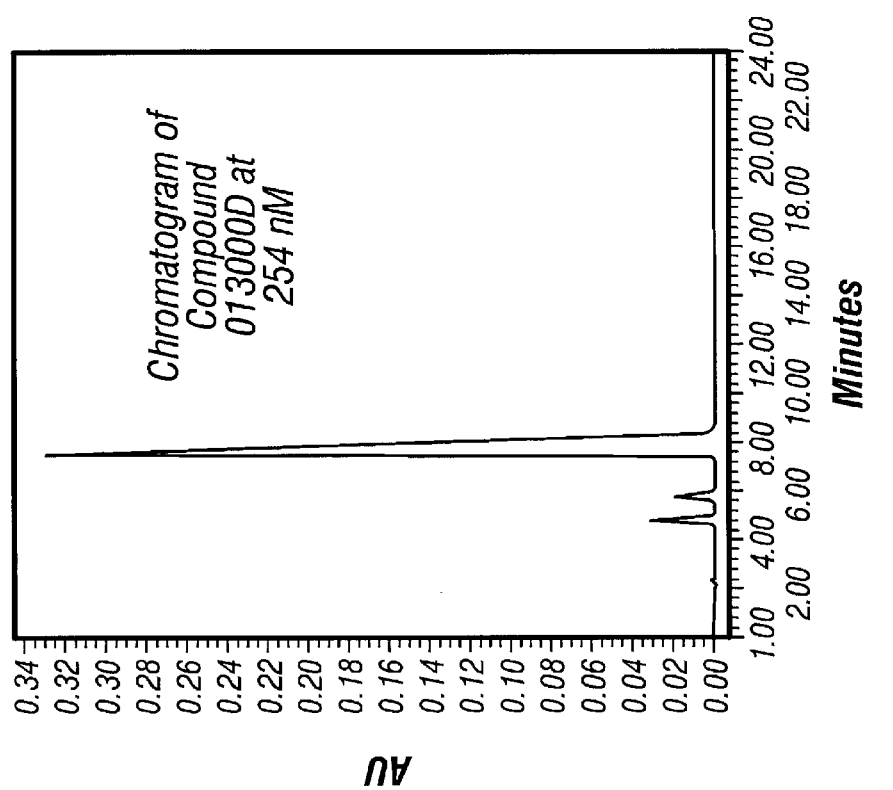

FIG. 2 shows alternative pathways for synthesis of 8-nitroguanine. One pathway is to react guanine in DNA with peroxynitrite. This produces many products, one of which is 8-nitroguanine. An alternative pathway for synthesis of 8-nitroguanine, described above as Method 1, involves exposure of guanine to acetic anhydride in the presence of HNO3. The HPLC profile of the products of this reaction is shown in FIGS. 3A and 3B. The absorbance profiles for eluting peaks are shown at 254 nm (FIG. 3A) and 380 nm (FIG. 3B). At 380 nm, a single peak is observed, with a retention time of 7.98 min. At 254 nm, two additional minor peaks were observed at lower elution volumes.

Figure 4:
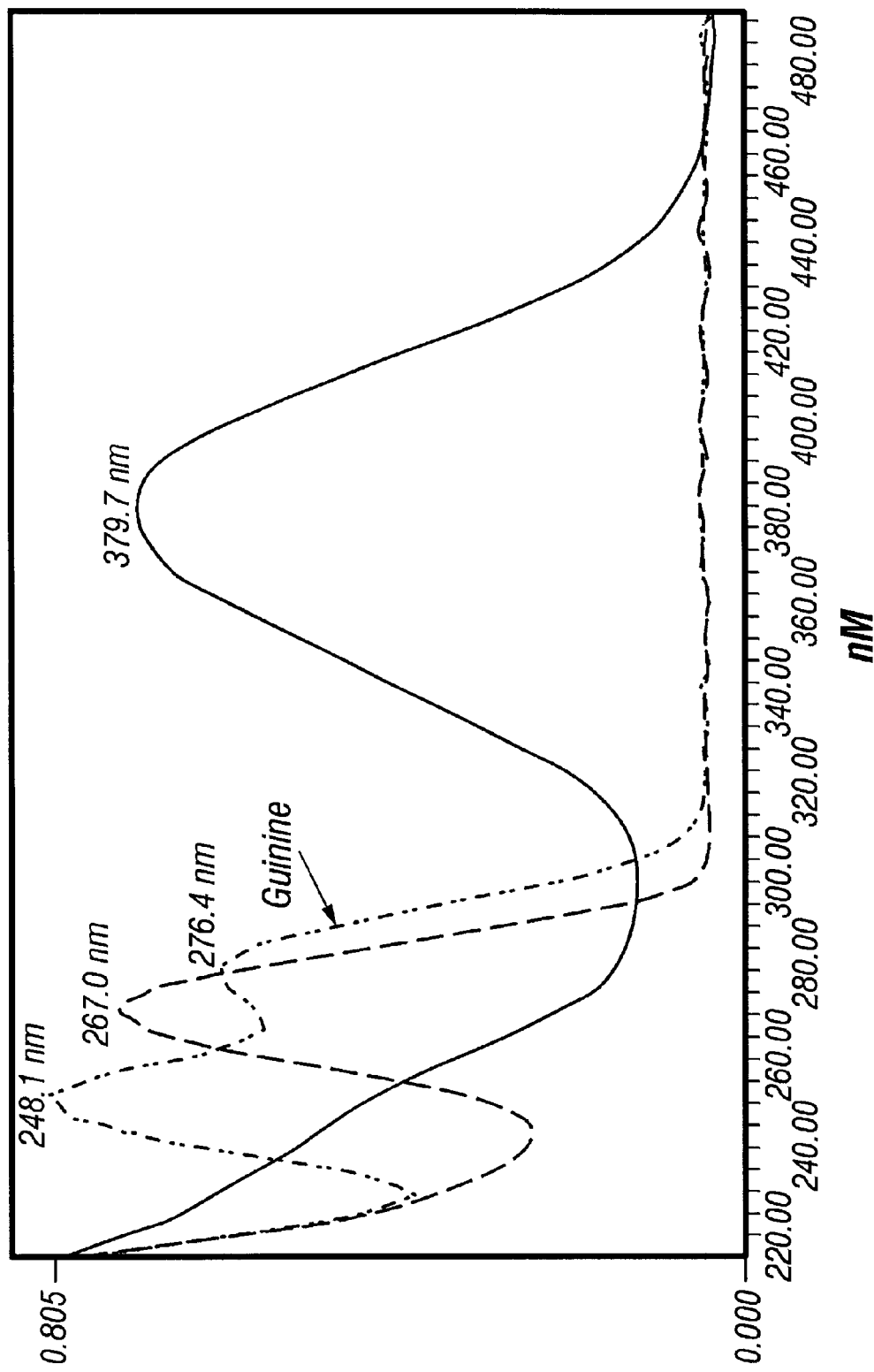
FIG. 4 shows the absorbance profiles of peaks resulting from exposure of guanine to acetic anhydride and nitric acid.

FIG. 4 shows the absorbance profile for the products of the synthetic reaction of Method 1. Three compounds are present, corresponding to the three peaks observed at 254 nm. The absorbance spectrum of the major peak eluting at 7.98 minutes is indicated by the solid line in FIG. 4. Based on its similarity with previously published absorbance profiles (Yermilov et al., 1995b; Byun et al., 1999) this peak was tentatively identified as 8-nitroguanine. Another compound, eluting at 4.99 minutes, showed an absorbance profile very similar to guanine, as indicated in FIG. 4. The identity of the third minor peak, eluting at 5.86 minutes, is presently unknown. These results suggested that Method 1 produced only two reaction products, with the major component tentatively identified as 8-nitroguanine.

Although the major peak from Method 1 showed an absorbance profile similar to 8-nitroguanine, these results were not confirmed by mass spectrometry analysis. The molecular weight of 8-nitroguanine should be 197. The molecular weight of the major product of Method 1 was determined by mass spectrometry to be 198, the same as 8-nitroxanthine. It is thus believed that the major reaction product of Method 1 was 8-nitroxanthine.

Method 3 was a modification of Method 1, performing the reaction in acetonitrile instead of acetic anhydride as the solvent. Method 4 was a modification of Method 3, using nitronium tetrafluoroborate as the nitrating agent in acetonitrile solvent, without any acid addition.

Figure 5B:
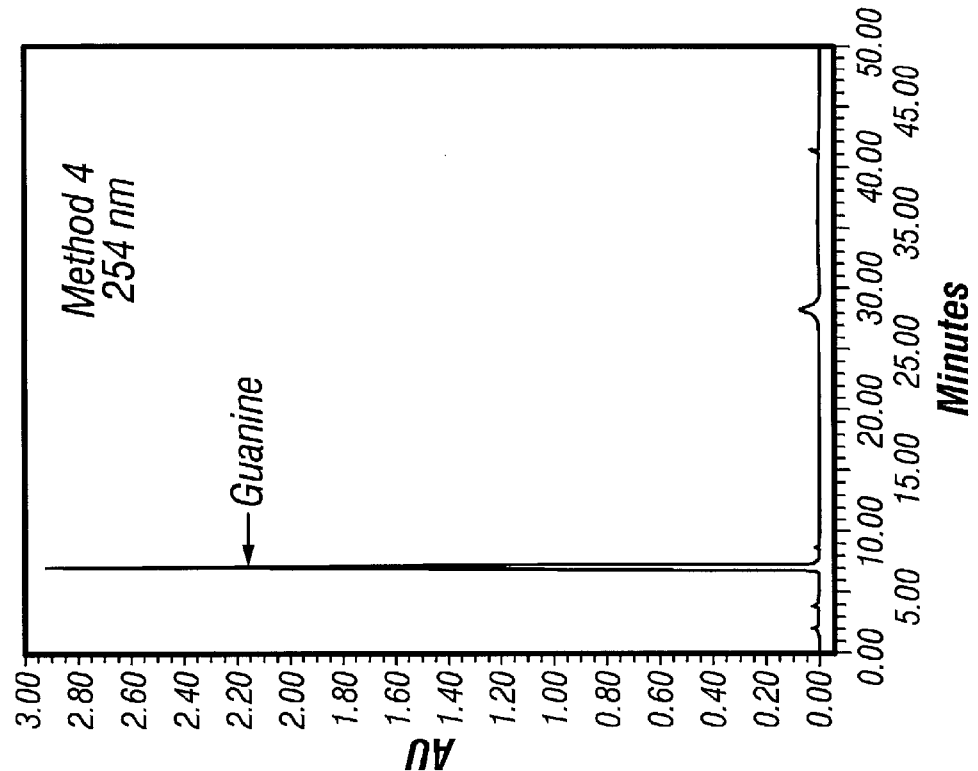
FIG. 5B shows the chromatogram for the products of synthetic method 4, detected at 254 nm.
Figure 5A:
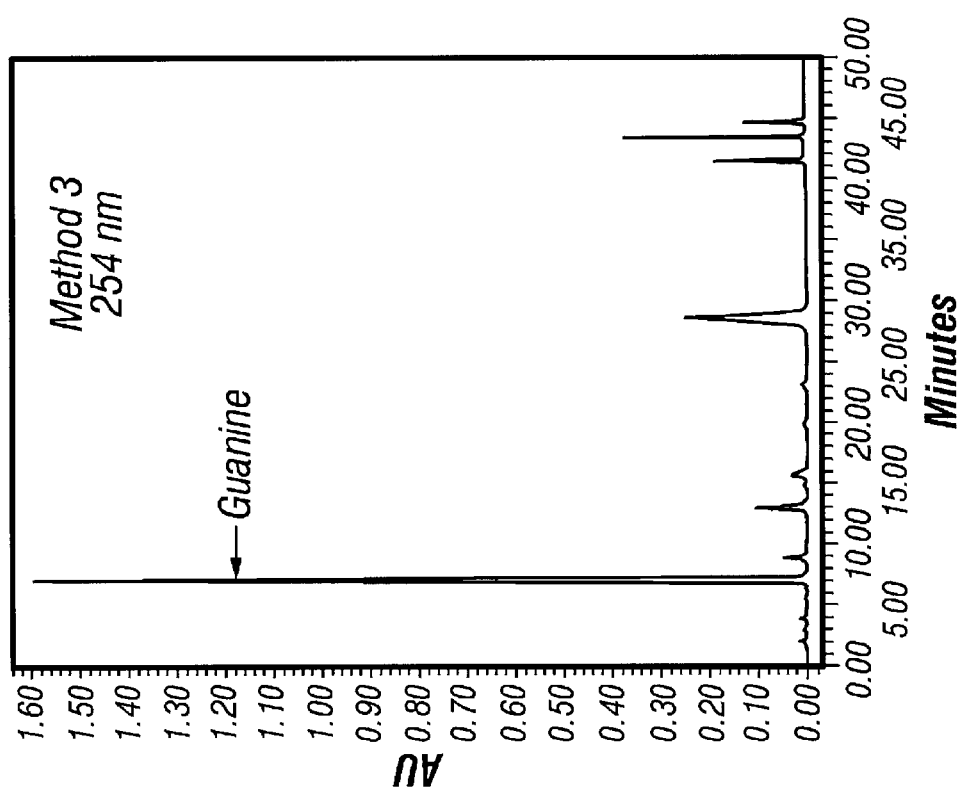
FIG. 5A shows the chromatogram for the products of synthetic method 3, detected at 254 nm.
Figures 5C, 5D:
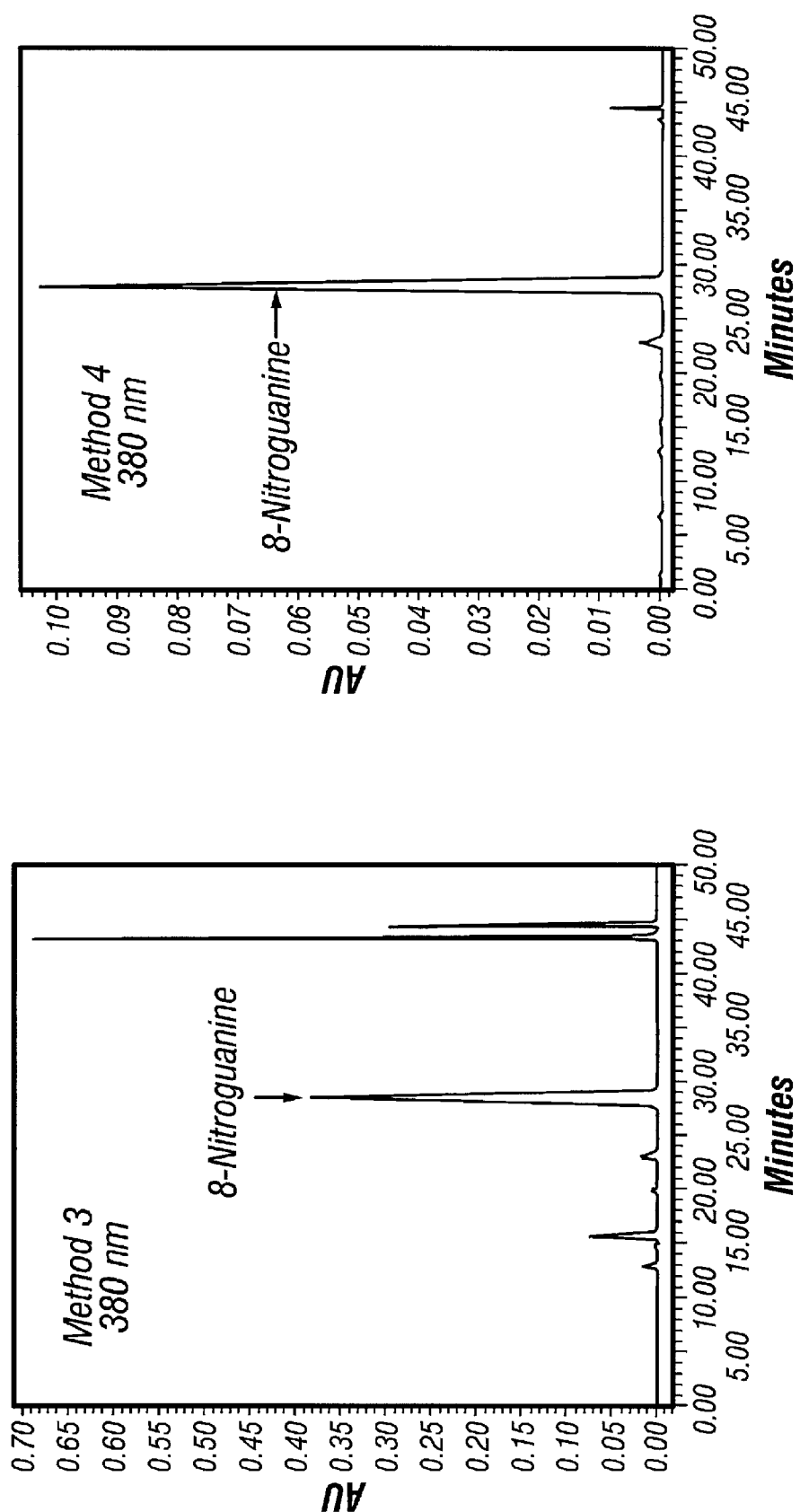
FIG. 5C shows the chromatogram for the products of synthetic method 3, detected at 380 nm.
FIG. 5D shows the chromatogram for the product of synthetic method 4, detected at 380 nm.

FIG. 5 shows the HPLC chromatograms for the reaction products of Methods 3 and 4. FIG. 5A shows the reaction products of Method 3 at 254 nm. FIG. 5B shows the reaction products of Method 4 at 254 nm. FIGS. 5C and 5D show, respectively, the reaction products of Methods 3 and 4 at 380 nm. Both Methods 3 and 4 resulted in peaks apparently corresponding to 8-nitroguanine, which was a major peak in both chromatograms absorbing at 380 nm. However, Method 3 also resulted in several late eluting peaks of unknown identity.

Mass spectrometry was performed on the putative 8-nitroguanine peaks obtained from Method 3 and Method 4. Both compounds showed a molecular weight of 197, confirming the identification of the peak as 8-nitroguanine. Although 8-nitroguanine was formed by these protocols, the absorbance spectra at 254 nm indicates that the reaction was not particularly efficient.

Figure 6:
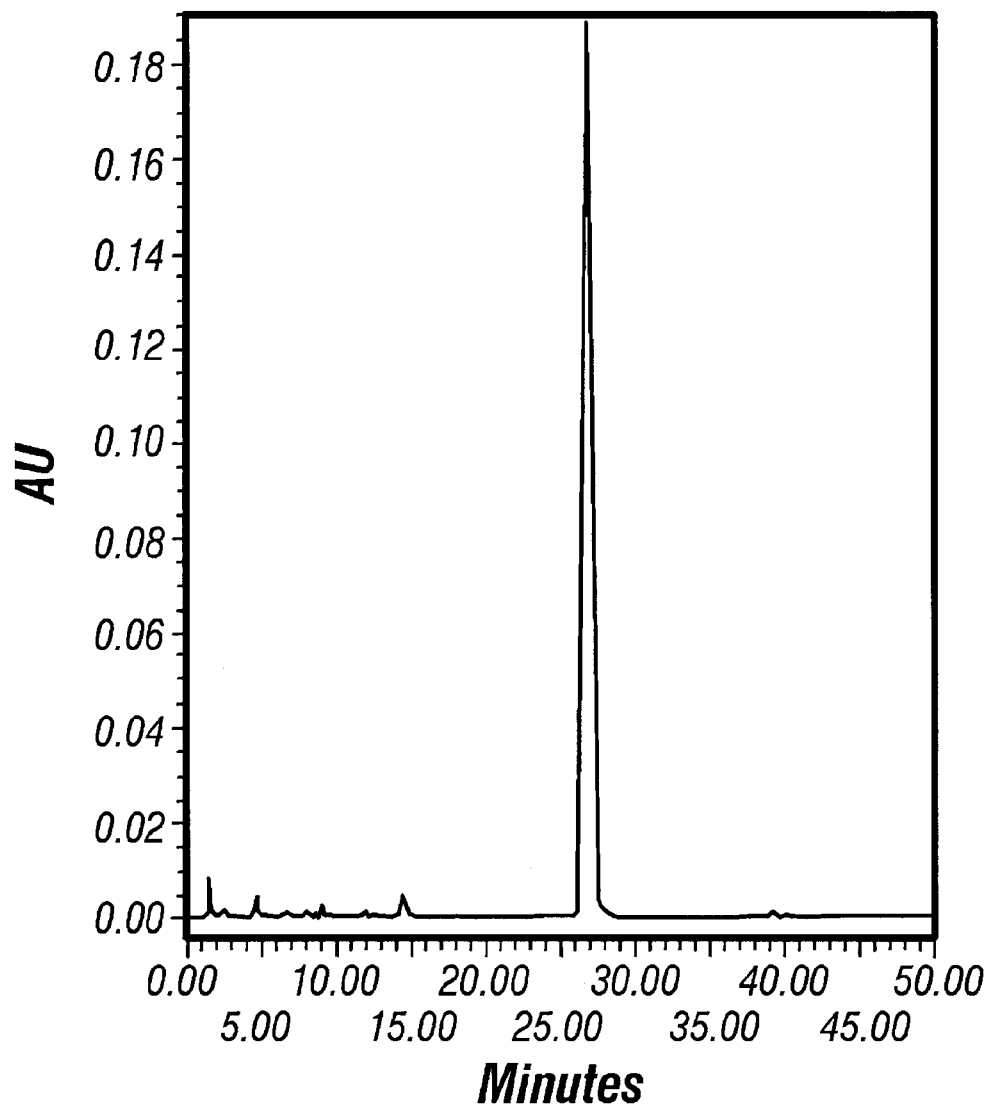
FIG. 6 shows the chromatogram for the products of synthetic method 5, detected at 380 nm.

In Method 5 the acetic anhydride of Method 1 was replaced with trifluoroacetic anhydride. FIG. 6 shows an HPCL chromatogram for the products of Method 5. One major peak at 380 nm was detected, with a retention time almost identical to the 8-nitroguanine produced by Methods 3 and 4. The absorbance profile of the Method 5 peak was also very similar to 8-nitroguanine (not shown). Contaminating peaks were almost negligible at 380 nm (FIG. 6).

Figure 7B:
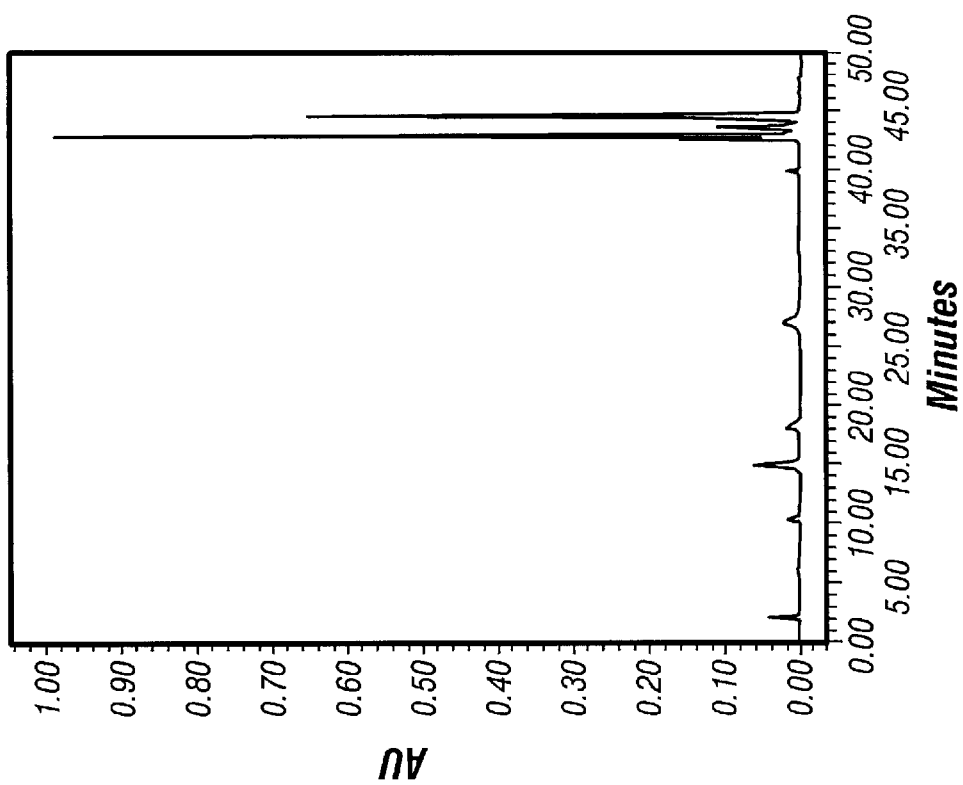
FIG. 7B shows the chromatogram for the products of synthetic method 6, using water as the solvent.
Figure 7A:
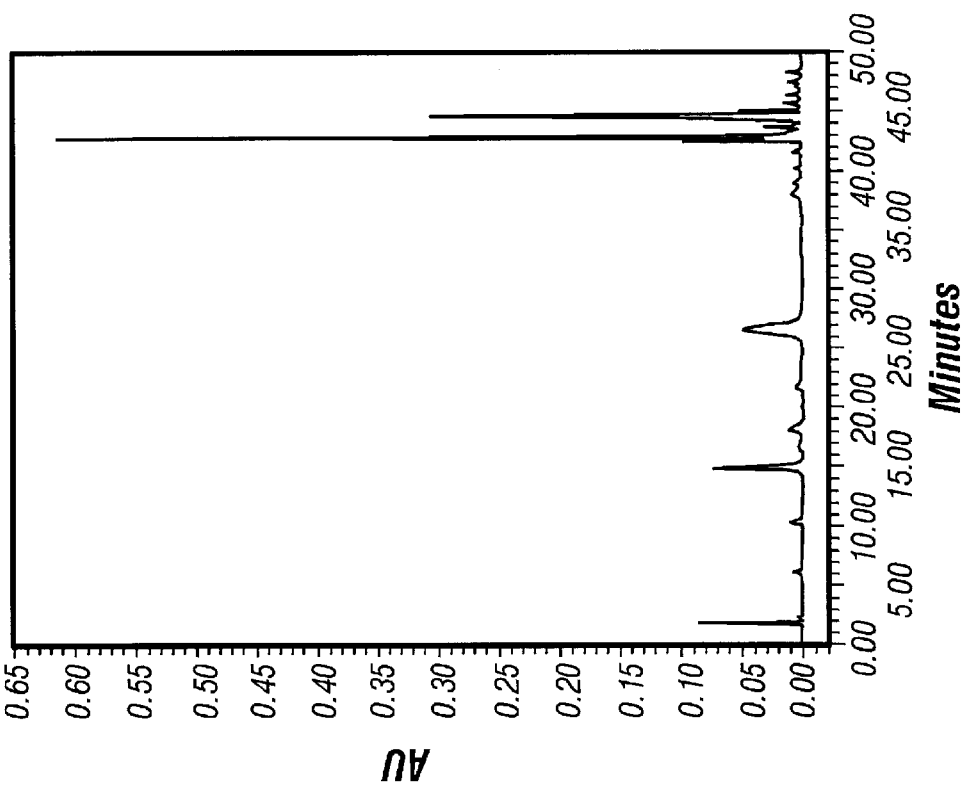
FIG. 7A shows the chromatogram for the products of synthetic method 6, using dimethlyformamide as the solvent.

Method 6 showed by comparison the results of reaction of 8-bromoguanine with sodium nitrite, using either water or dimethylformamide as a solvent. The HPLC chromatograms for the products of Method 6 are shown in FIG. 7, with either dimethlyformamide (FIG. 7A) or water (FIG. 7B) as the solvent. While a peak corresponding to 8-nitroguanine can be found in both the water and DMF reactions, there were numerous contaminating peaks as well.

Figure 8B:
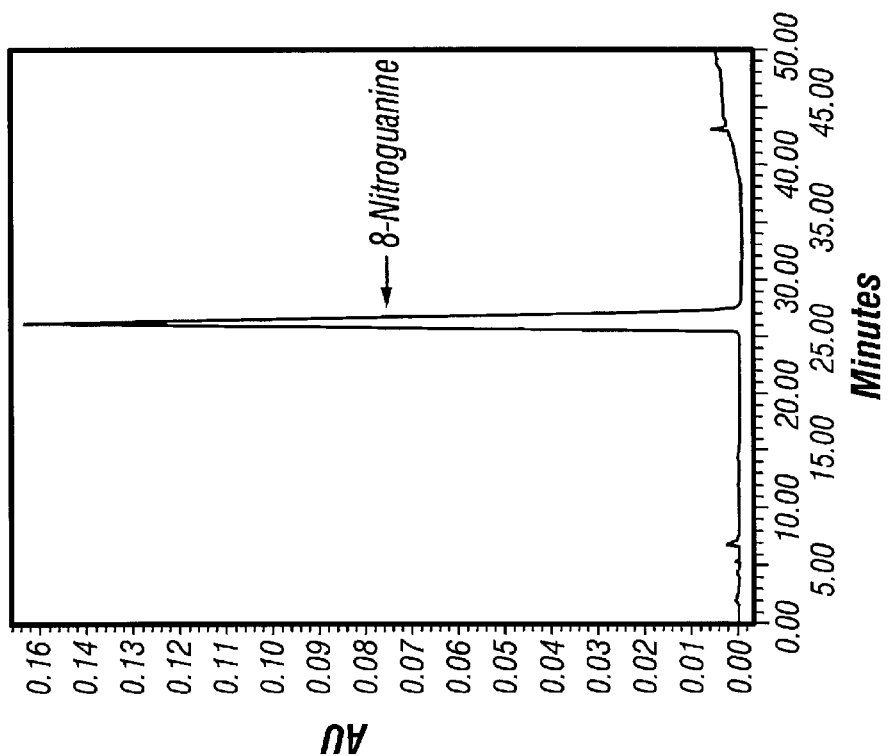
FIG. 8B shows the chromatogram for the products of synthetic method 4, using a long reaction time followed by extraction with HCl and detected at 254 nm.
Figure 8A:
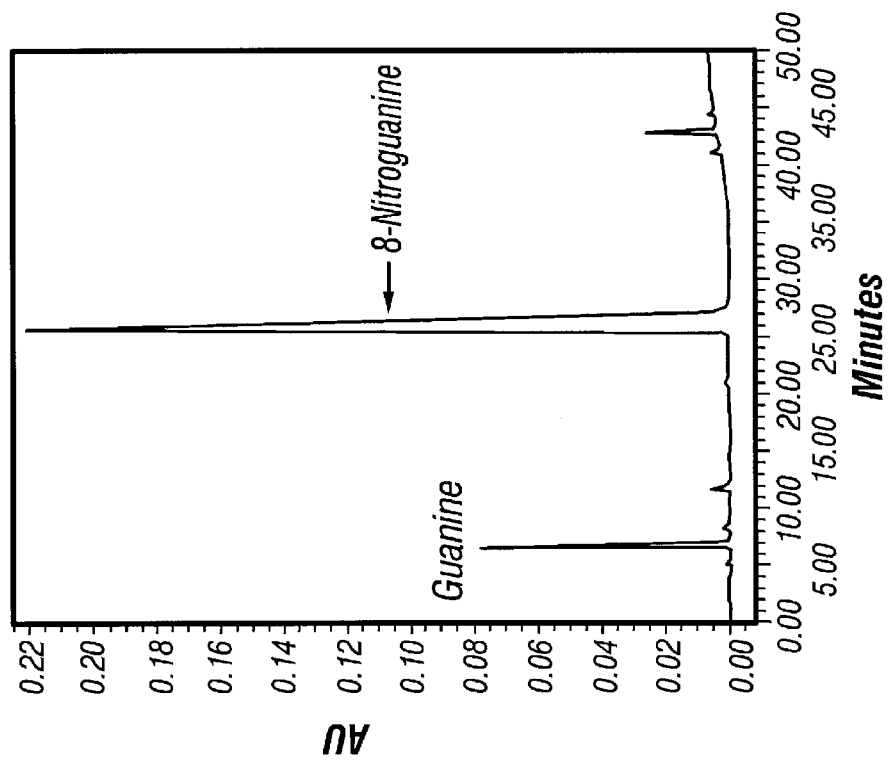
FIG. 8A shows the chromatogram for the products of synthetic method 4, using a long reaction time and detected at 254 nm.
Figure 8D:
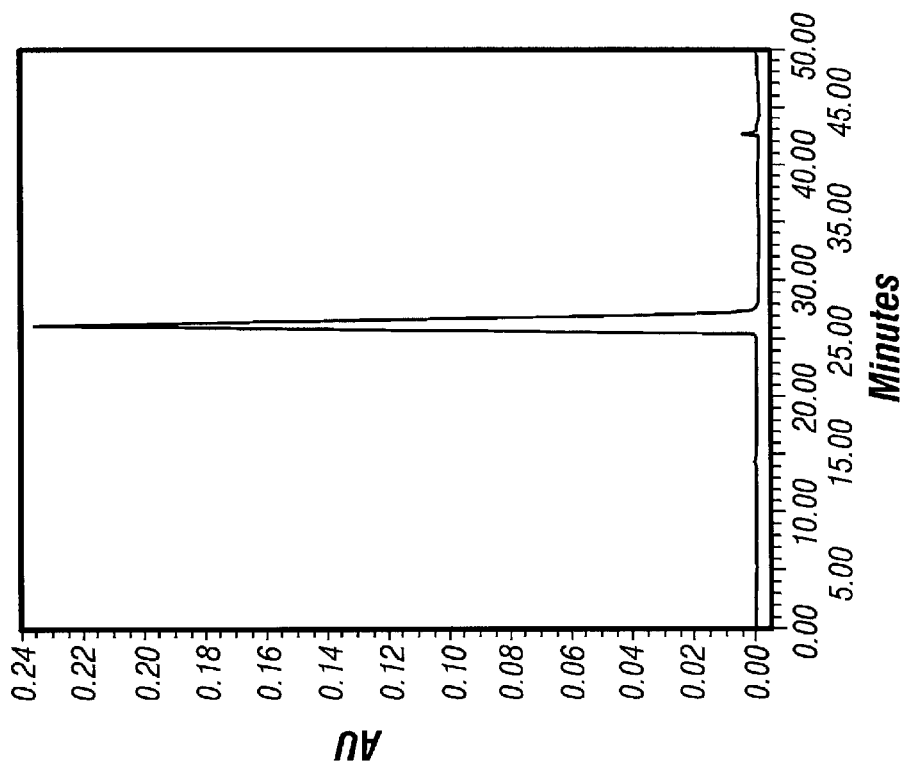
FIG. 8D shows the chromatogram for the products of synthetic method 4, using a long reaction time followed by extraction with HCl and detected at 380 nm.
Figure 8C:
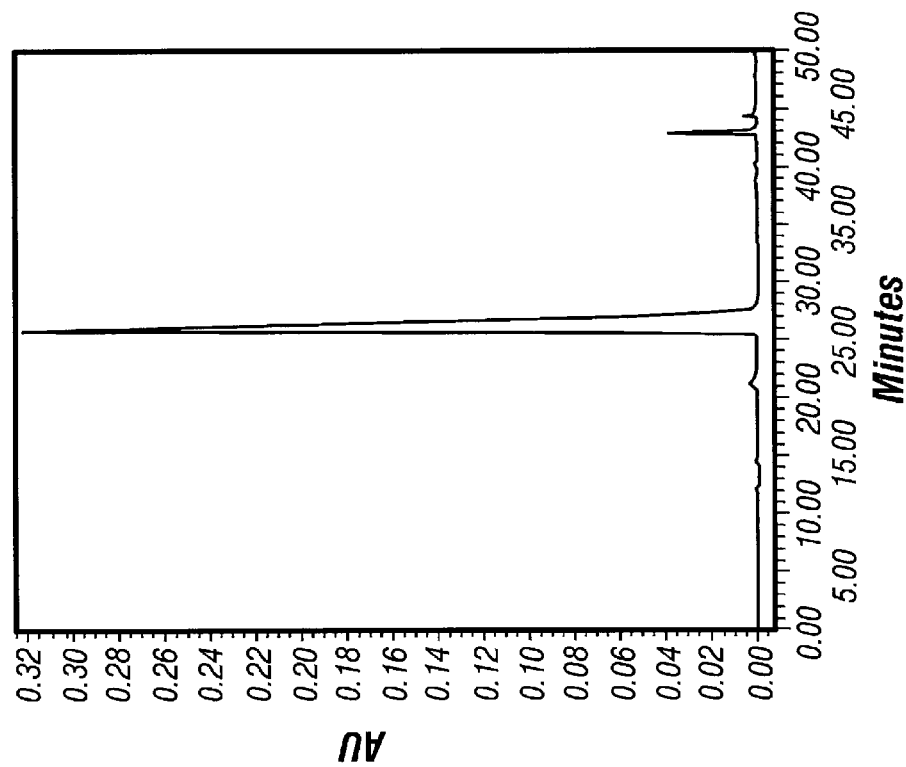
FIG. 8C shows the chromatogram for the products of synthetic method 4, using a long reaction time and detected at 380 nm.

Method 4 was further improved in an attempt to obtain a pure preparation of 8-nitroguanine. The improved Method 4 continued to use acetonitrile as solvent, but the molar ratio of nitronium tetrafluoroborate to guanine was increased from 1:1 to 2:1 and the mixture was refluxed for 12 hours. After 12 hours of refluxing, a yellow precipitate had formed in the flask. This precipitate was further purified by boiling in 1 M HCl, resulting in an extracted precipitate consisting of material that was insoluble in hot HCl. The HPLC chromatograms for the reaction products of improved Method 4 are shown in FIG. 8. FIG. 8A shows the chromatogram at 254 nm using the long reaction time Method 4. FIG. 8B shows the chromatogram at 254 nm of the HCl extracted precipitate. FIG. 8C shows the chromatogram at 380 nm of the long reaction time Method 4. FIG. 8D shows the HCl extracted precipitate at 380 nm. It is apparent from FIGS. 8B and 8D that the acid extracted precipitate contained an almost pure preparation of 8-nitroguanine.

In summary, the improved method 4 appears to give an almost pure preparation of 8-nitroguanine.

Example 3

Detection of 8-Nitroguanine in Urine Samples

In certain embodiments, 8-nitroguanine is detected in samples, preferably urine or blood samples, from organ transplant recipients or individuals exposed to environmental stress, such as infection or ionizing radiation. The present example demonstrates that 8-nitroguanine is detectable in urine samples from an individual with a chronic infection.

Sample Treatment

Fresh urine samples were collected and stored on ice prior to use. The samples were split into four 5 ml aliquots. Samples were treated by addition of 0.5 ml of concentrated hydrochloric acid or 0.5 ml of 37% ammonia. The pH of the acidified sample was less than 1.0. Certain samples were spiked with 8-nitroguanine as an internal control. Addition of acid or base to urine frequently resulted in the formation of a precipitate. Methylene chloride (5 ml) was added to remove organic-soluble contaminants and the tubes were vigorously shaken. Some tubes were also treated by addition of 1 ml of saturated NaCl solution before shaking. Samples were immediately centrifuged at 2,500 rpm for 20 min in a clinical centrifuge to separate the organic and aqueous phases. The organic phase was discarded and the aqueous phase was collected for analysis. Before HPLC chromatography, the pH was adjusted to 4.0 and methanol was added to 4% (vol/vol). Samples were filtered through 0.2 $\mu$m nitrocellulose syringe-tip filters before injection of 0.1 ml aliquots into the HPLC.

Detection of 8-Nitroguanine

Samples were analyzed by reverse-phase HPLC, as described above, with the following changes. A C18 Medichem (Woodridge, Ill.) reverse-phase column was used, resulting in a decrease in total run time to 37 min. The run conditions used were: 0 to 18 min (20 mM ammonium formate, pH 4.0, 4% methanol); 18 to 25 min (20 mM ammonium formate, pH 4.0, 30% methanol) and 25 to 37 min (20 mM ammonium formate, pH 4.0, 4% methanol). Eluting peaks were detected using an ESA CoulArray electrochemical coulometric array detector (Chelmsford, Mass.). The electrochemical detector was more sensitive to 8-nitroguanine than UV detectors.

Results

Figure 9:
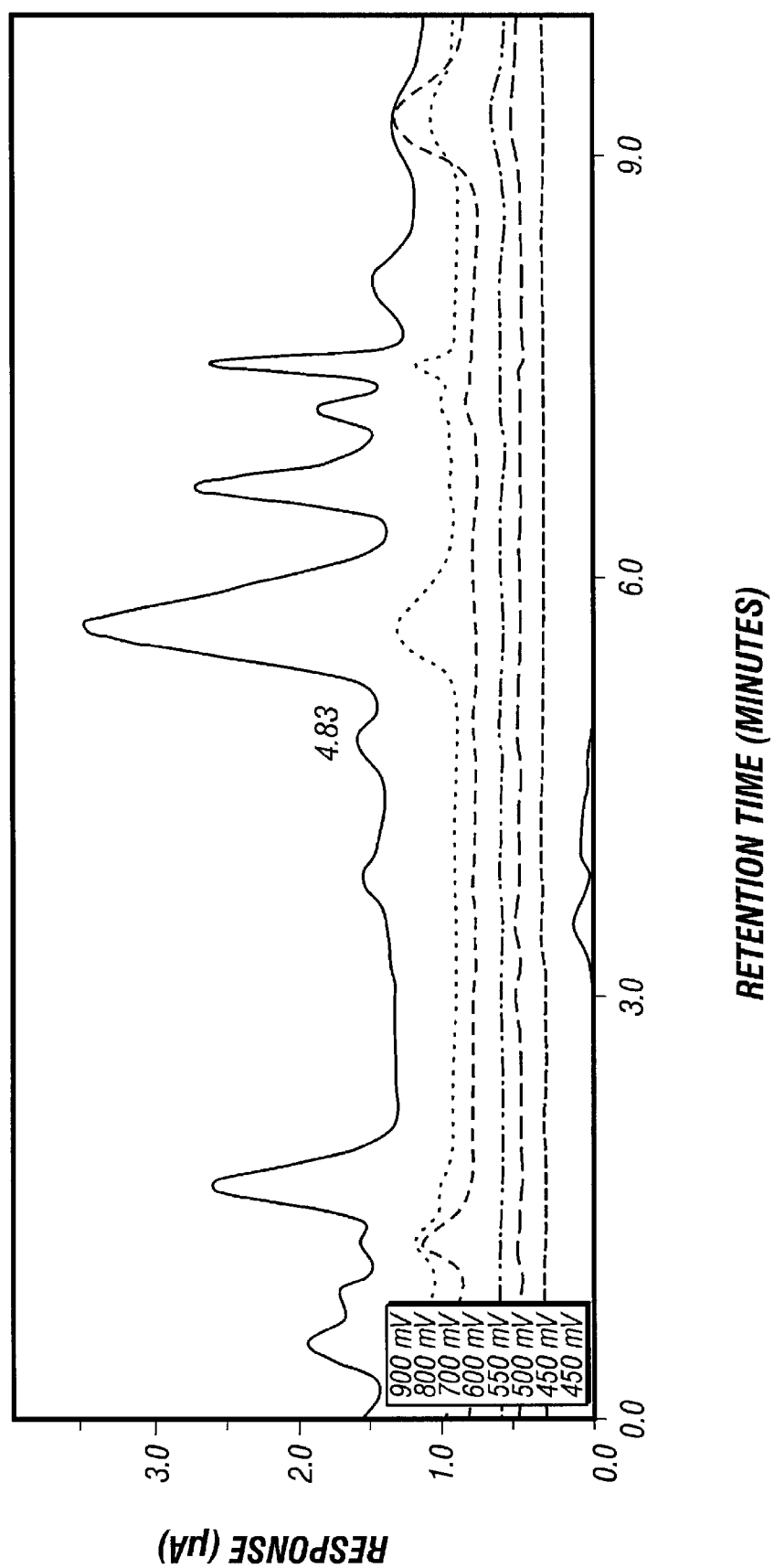
FIG. 9 shows a representative chromatogram for a urine sample from a patient with a chronic infection. A peak eluting at 4.83 minutes is marked.

FIG. 9 shows the results of HPLC analysis of a representative urine sample from a patient with a chronic infection. The samples was treated with base (ammonia), then neutralized to pH 4.0 as disclosed above. A peak identified in FIG. 9 as eluting at 4.83 min corresponded to the elution time of the 8-nitroguanine internal standard (not shown). These results show that 8-nitroguanine can be detected in the urine of a patient with chronic infection, corresponding to an environmental stress.

All of the COMPOSITIONS, METHODS and APPARATUS disclosed and claimed herein can be made and executed without undue experimentation in light of the present disclosure. While the compositions and methods of this invention have been described in terms of preferred embodiments, it will be apparent to those of skill in the art that variations may be applied to the COMPOSITIONS, METHODS and APPARATUS and in the steps or in the sequence of steps of the methods described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Burney et al., "The chemistry of DNA damage from nitric oxide and peroxynitrite," *Mutation Res.* 424:37–49, 1999.

Byun, J., Henderson, J. P., Mueller, D. M., and Heinecke, J. W., "8-Nitro-2'deoxyguanosine, a Specific Marker of Oxidation by Reactive Nitrogen Species, is Generated by the Myeloperoxidase-Hydrogen Peroxide-Nitrite System of Activated Human Phagocytes," Biochemistry, 38:2590–2600, 1999

Diplock et al., *Brit. J. Nutrition* 80(Suppl. 1):S77–S112, 1998.

Douki et al., *Chem. Res. Toxicol.* 9:3–7, 1996.

Effenhauser, et al *Anal. Chem.,* 66:2949–2953, 1994.

Effenhauser, et al. *Anal. Chem.,* 65:2637–2642, 1993.

Fodor et al., Multiplexed biochemical assays with biological chips. *Nature* 364, 555–556, 1993

Freifelder, *Physical Biochemistry Applications to Biochemistry and Molecular Biology,* 2nd ed. Wm. Freeman and Co., New York, N.Y., 1982.

Froehler, B., et al. *Nucleic Acids Research,* 16:4831–4839, 1988.

Froehler, B., et al. *Nucleosides and Nucleotides,* 6:287–291, 1987.

Froehler, B., et al., *Nucleic Acids Research,* 14:5399–5467, 1986b.

Froehler, B., *Tet Lett.* 27:5575–5578, 1986a.

Fukuyama et al., *Free Radical Biol. & Med.* 22:771–774, 1997.

Hacia et al., *Nature Genetics,* 14:441–447, 1996

Harrison et al., *Science,* 261:895–897, 1993.

Hughes, "Relationships between nitric oxide, nitroxyl ion, nitrosonium cation and peroxynitrite," *Biochim. Biophys. Acta* 1411:263–272, 1999.

Hurst and Lymar, "Toxicity of peroxynitrite and related reactive nitrogen species towards *Escherichia coli,"* *Chem. Res. Toxicol.* 10:802–810, 1997

Jacobson et al., *Anal. Chem.,* 66:1107–1113, 1994.

Jayasena, S. D., Aptamers: An Emerging Class of Molecules That Rival Antibodies in Diagnostics. *Clin. Chem.* 45: 1628–1650, 1999.

Lipshutz et al., Using oligonucleotide probe arrays to access genetic diversity. *Biotechniques* 19: 442–447, 1995.

Lorsch and Szostak, In vitro selection of nucleic acid sequences that bind small molecules. In: *Combinatorial Libraries: Synthesis, Screening and Application Potential.* (R. Cortese, ed.) Walter de Gruyter Publishing Co., New York, pp. 69–86, 1996.

Love, "Oxidative stress in neurological disease," *Brain Pathol.* 9:119–131, 1999.

Manz, et al., *J. Chromatogr.,* 593:253–258, 1992.

Matson et al., Biopolymer synthesis on polypropylene supports: oligonucleotide arrays. *Anal. Biochem.* 224: 110–116, 1995.

PCT App. No. WO 91/19813

PCT App. No. WO 94/05414

Pease et al., Light-generated oligonucleotide arrays for rapid DNA sequence analysis. *Proc. Natl. Acad. Sci. USA* 91: 5022–26, 1994.

Schwemmer et al., *Clin. Chim. Acta* 297:207–216, 2000.

Shoemaker et al., *Nature Genetics* 14:450–456, 1996.

Southern et al., Arrays of complementary oligonucleotides for analyzing the hybridization behaviour of nucleic acids. *Nucleic Acids Res.* 22: 1368–73, 1994.

Spencer, J. P. E., Wong, J., Jenner, A., Aruoma, 0. 1., Cross, C. E., and Halliwell, "Base Modification and Strand Breakage in Isolated Calf Thymus DNA and in DNA from Human Skin Epidermal Keratinocytes Exposed to Peroxynitrite or 3-Morpholinosydnonimine," Chemical Research in Toxicology, 9(1996), pl 152–1158.

Travis, Chips ahoy: microchips covered with DNA emerge as powerful research tools. *Science News* 151: 144–45, 1997.

Tretyakova et al., "Peroxynitrite-induced DNA damage in the supF gene: correlation with the mutational spectrum," *Mutation Res.* 447:287–303, 2000.

Tsuda et al., *Anal. Chem.,* 62:2149–2152, 1990.

Tuo et al., "importance of guanine nitration and hydroxylation in DNA in vitro and in vivo," *Free Radical Biol. & Med.* 29:147–155, 2000.

U.S. Pat. No. 5,270,163
U.S. Pat. No. 5,296,375
U.S. Pat. No. 5,304,487
U.S. Pat. No. 5,475,096
U.S. Pat. No. 5,484,707
U.S. Pat. No. 5,578,832
U.S. Pat. No. 5,582,981
U.S. Pat. No. 5,595,877
U.S. Pat. No. 5,637,459
U.S. Pat. No. 5,837,832
U.S. Pat. No. 5,837,860
U.S. Pat. No. 5,856,174
U.S. Pat. No. 5,861,242
U.S. Pat. No. 5,904,824
U.S. Pat. No. 6,093,723
U.S. Pat. No. 6,113,898
U.S. Pat. No. 6,133,324
U.S. Pat. No. 6,200,978

Woolley and Mathies, *Proc Natl Acad Sci USA,* 91:11348–52, 1994

Yermilov, V., Rubio J., and Ohshima, H., "Formation of 8-nitroguanine in DNA treated with peroxynitrite in vitro and its rapid removal from DNA by depurination." FEBS Letters, 376:207–210, 1995a.

Yermilov, V., Rubio J., Becchi, M., Friesen, M. D., Pignatelli, B., and Ohshima, H., "Formation of 8-nitroguanine by the reaction of Guanine with peroxynitrite in vitro," Carcinogenesis 16:2045–2050, 1995b.

Yermilov, V., Yoshie, Y., Rubio J., and Ohshima, H., "Effects of carbon dioxide/bicarbonate on induction of DNA single-strand breaks and formation of 8-nitroguanine, 8-oxoguanine and base-propenal mediated by peroxyn it rite," FEBS Letters, 399:67–70, 1996.

What is claimed is:

1. A method of predicting organ rejection in a transplant recipient comprising:

a) collecting one or more samples from said recipient;
b) detecting 8-nitroguanine in said one or more samples; and
c) determining likelihood of organ rejection by the presence of a spike or sustained elevated level of 8-nitroguanine in said samples.

2. The method of claim 1, wherein said sample is a urine sample, a blood sample or a biopsy sample.

3. The method of claim 1, wherein said detecting step comprises HPLC, mass-spectroscopy, gas chromatography, nuclear magnetic resonance, capillary electrophoresis or electrochemical detection.

4. A method of determining exposure to environmental stressors selected from the group consisting of ionizing radiation, toxic chemicals and infectious agents in a organism comprising:
a) collecting one or more samples from said organism;
b) detecting 8-nitroguanine in said one or more samples; and
c) determining short-term exposure to said environmental stressors by a spike in 8-nitroguanine in said sample or chronic exposure to said environmental stressors by long-term elevation of 8-nitroguanine levels in said sample.

5. The method of claim 4, wherein said sample is a blood sample, a urine sample or a biopsy sample.

* * * * *